United States Patent [19]

Fujiwara et al.

[11] Patent Number: 6,150,371
[45] Date of Patent: Nov. 21, 2000

[54] METHOD FOR PREVENTING AND FOR TREATING AUTOIMMUNE DISEASE

[75] Inventors: Toshihiko Fujiwara, Ebina; Shinichi Kurakata, Yokohama; Takashi Fujita, Kashiwa; Tsunemichi Hosokawa, Kanagawa; Junichiro Fukushige; Hiroyoshi Horikoshi, both of Funabashi, all of Japan

[73] Assignee: Sankyo Company, Limited, Tokyo, Japan

[21] Appl. No.: 09/201,477

[22] Filed: Nov. 30, 1998

Related U.S. Application Data

[63] Continuation of application No. PCT/JP97/01827, May 29, 1997.

[30]  Foreign Application Priority Data

| May 31, 1996 | [JP] | Japan | 8-138667 |
| Jul. 11, 1996 | [JP] | Japan | 8-181850 |
| Nov. 29, 1996 | [JP] | Japan | 8-319225 |

[51] Int. Cl.$^7$ .......................... A61K 45/00; A61K 31/42; A61K 31/425

[52] U.S. Cl. .......................... 514/256; 514/258; 514/299; 514/300; 514/303; 514/336; 514/340; 514/341; 514/342; 514/352; 514/357; 514/359; 514/369; 514/370; 514/376; 514/377; 514/380; 514/393; 514/394; 514/413; 514/414; 514/415; 514/416; 514/419; 514/438; 514/444; 514/825; 514/885; 514/866

[58] Field of Search .......................... 514/256, 258, 514/299, 300, 303, 336, 340, 341, 342, 352, 357, 359, 369, 370, 376, 377, 380, 393, 394, 413, 414, 415, 416, 419, 438, 444, 825, 885, 866

[56]  References Cited

U.S. PATENT DOCUMENTS

| 4,287,200 | 9/1981 | Kawamatsu et al. . |
| 4,340,605 | 7/1982 | Kawamatsu et al. . |
| 4,438,141 | 3/1984 | Kawamatsu et al. . |
| 4,444,779 | 4/1984 | Kawamatsu et al. . |
| 4,461,902 | 7/1984 | Kawamatsu et al. . |
| 4,572,912 | 2/1986 | Yoshioka et al. . |
| 4,687,777 | 8/1987 | Meguro et al. . |
| 4,703,052 | 10/1987 | Eggler et al. . |
| 4,725,610 | 2/1988 | Meguro et al. . |
| 4,873,255 | 10/1989 | Yoshioka et al. . |
| 4,897,393 | 1/1990 | Iijima et al. . |
| 4,897,405 | 1/1990 | Alessi et al. . |
| 4,898,694 | 2/1990 | Schwartz et al. ............. 260/397.5 |
| 4,918,091 | 4/1990 | Cantello et al. . |
| 4,948,900 | 8/1990 | Iijima et al. . |
| 5,002,953 | 3/1991 | Hindley . |
| 5,061,717 | 10/1991 | Clark et al. . |
| 5,120,754 | 6/1992 | Clark et al. . |
| 5,132,317 | 7/1992 | Cantello et al. . |
| 5,194,443 | 3/1993 | Hindley . |
| 5,223,522 | 6/1993 | Clark et al. . |
| 5,232,925 | 8/1993 | Hindley . |
| 5,260,445 | 11/1993 | Hindley . |
| 5,550,166 | 8/1996 | Ostlund et al. . |
| 5,594,015 | 1/1997 | Kurtz et al. ............. 514/369 |
| 5,866,595 | 2/1999 | Pershadsingh et al. ............. 514/369 |

FOREIGN PATENT DOCUMENTS

| 332332 | 9/1989 | European Pat. Off. . |
| 604983 | 7/1994 | European Pat. Off. . |
| 676398 | 10/1995 | European Pat. Off. . |
| 708098 | 4/1996 | European Pat. Off. . |
| 745600 | 12/1996 | European Pat. Off. . |
| 4-69383 | 3/1992 | Japan . |
| WO 89/08651 | 9/1989 | WIPO . |
| WO 91/07107 | 5/1991 | WIPO . |
| WO 9112003 | 8/1991 | WIPO . |
| WO 92/02520 | 2/1992 | WIPO . |
| WO 94/01433 | 1/1994 | WIPO . |
| WO 95/18125 | 7/1995 | WIPO . |
| WO 9634943 | 11/1996 | WIPO . |
| WO 99/06059 | 2/1999 | WIPO . |

OTHER PUBLICATIONS

Chemical Abstract 97:156763, "Therapeutic Effects of of Dehydroepiandrosterone (DHEA) in Diabetic Mice", Sep. 1982.

Konnichinochiryoushishin, Igaku Shoin, p. 577 (1996) (Collagen Diseases (Connective Tissue Diseases))*.

Byourigakutaikei, Suppl. 1, pp. 91–105 (1995) (Immunotoxicity and Autoimmunity)*.

Tounyoubyou, vol. 37, No. 2, pp. 127–129 (1994) (Study of Inhibition of the Onset of Type I Diabetes By CS–045)*.

N. Yagi et al., "Expression of Intercellular Adhesion Molecule 1 on Pancreatic β–Cell Accelarates β–Cell Destruction by Cytotoxic T–Cells in Murine Autoimmune Diabetes", *Diabetes*, 44, 744–752 (1995).

J.L. Baron et al., "The Pathogenesis of Adoptive Murine Autoimmune Diabetes Requirea An Interaction Between α4–Integrins and Vascular Cell Adhesion Molecule–1", *J. Clin. Invest.*, 93, 1700–1708 (1994).

T. Fujiwara et al., "Characterization of New Oral Anidiabetic Agent CS–045", *Diabetes*, 37, 1549–1558 (1988).

C. Hofmann and J.R. Colca, "New Oral Thiazolidinedione Antidiabetic Agents Act as Insulin Sensitizers", *Diabetic Care*, 15, 1075–1078 (1992).

C.V. Winder et al., "Comparative Bioassays of Drugs in Adjuvant–Induced Arthritis in Rats: Flufenamic Acid, Mefenamic Acid and Phenylbutazone", *Arthritis and Rheumatism*, 12, 472–482 (1969).

*Primary Examiner*—Frederick Krass
*Attorney, Agent, or Firm*—Frishauf, Holtz, Goodman, Langer & Chick, P.C.

[57]  ABSTRACT

A method for preventing or treating autoimmune diseases (excluding type I diabetes) by administering an insulin resistance improving substance as an active ingredient.

64 Claims, 3 Drawing Sheets

METHOD FOR PREVENTING AND FOR TREATING AUTOIMMUNE DISEASE

This application is a continuation application of International application PCT/JP97/01827 filed May 29, 1997.

The present invention relates to compositions for the treatment or prevention of autoimmune diseases (excluding type I diabetes) containing as their active ingredient a substance that improves insulin resistance, their use for the preparation of pharmaceuticals for treatment or prevention of autoimmune diseases (excluding type I diabetes), or a treatment method or prevention method for autoimmune diseases (excluding type I diabetes) by administering pharmacologically effective amounts thereof to warm-blooded animals.

BACKGROUND OF THE INVENTION

Autoimmune diseases are believed to involve immune responses to the body's own components that are not observed under normal conditions, which result in a pathological state that causes various tissue disorders and/or functional disorders. Autoimmune diseases are broadly classified into systemic autoimmune diseases and organ-specific autoimmune diseases according to their characteristics. Typical examples of systemic autoimmune diseases include systemic lupus erythematosus and chronic rheumatoid arthritis. On the other hand, typical examples of organ-specific autoimmune diseases include Hashimoto's disease and juvenile-onset type diabetes.

The mechanism of cell tissue disorder is mainly classified into a disorder mechanism mediated by antibodies and immune complexes (referred to as the "humoral immunity-mediated disorder mechanism") and a disorder mechanism mediated by T-lymphocytes and other cells (Cell-mediated cytotoxicity, referred to as the "cellular immunity-mediated disorder mechanism"). In general, the humoral immunity-mediated disorder mechanism is considered to be important in systemic autoimmune diseases, while the cellular immunity-mediated disorder mechanism is considered to be important in organ-specific autoimmune diseases.

However, due to recent progress in the field of immunology, it has been clearly shown that in the cellular immunity-mediated disorder mechanism, in addition to cytotoxic cells consisting primarily of lymphocytes gathering near the target cells followed by ultimately making direct contact with the target cells to impair them, cytotoxic cells also release humoral factors such as inflammatory cytokines (such as TNF, IL-1 and LT) which indirectly impair the target cells as a result of their mediation. On the other hand, in the humoral immunity-mediated disorder mechanism as well, it has also been clearly shown that there is, for example, an antibody-dependent cell-mediated cytotoxicity (ADCC) mechanism in the case of the involvement of cells such as killer lymphocytes, neutrophils and platelets [Byourigakutaikei, Suppl. 1, pp. 91–105 (1995)].

Thus, in the target internal organ or target organ disorder mechanism in autoimmune diseases, regardless of whether they are systemic autoimmune diseases or organ-specific autoimmune diseases, invasion by cytotoxic cells consisting primarily of lymphocytes is considered to be important in terms of causing various tissue and functional disorders. For this reason, compounds that inhibit invasion of lymphocytes in the above-mentioned target internal organ or target organ are useful as agents for prevention or treatment of autoimmune diseases.

Steroids, non-steroidal anti-inflammatory agents, immunosuppressants and so forth are currently used in the treatment of autoimmune diseases [Konnichinochiryoushishin, Igaku Shoin, p. 577 (1996)]. In addition, agents that inhibit the production and action of inflammatory cytokines such as TNFα and IL-1 have recently been developed. Further, various types of mouse monoclonal antibodies to cell adhesion factors (such as ICAM-1 and VCAM-1) have been developed for the purpose of inhibiting the invasion of cytotoxic lymphocytes into the target internal organs and target organs. The therapeutic effects of these monoclonal antibodies have been reported in various animal models such as DBA/2 mice [Yagi, et al., Diabetes, 44, 744 (1995); Baron, et al., J. Clin. Invest., 93, 1700 (1994)]. However, none of these therapeutic agents or therapeutic methods exhibits adequate effects, and they also have the disadvantage of serious adverse effects. There is therefore the desire for a preventive or therapeutic agent for autoimmune diseases having excellent clinical efficacy and weaker adversity.

In recent years, substances that improve insulin resistance are known to function as agents for preventing or treating diabetes. Here, insulin resistance improving substances refer to compounds that improve impaired insulin action despite the presence of endogenous insulin. These substances that improve insulin resistance include a wide range of compounds. Typical examples include thiazolidinedione compounds, oxazolidinedione compounds, isoxazolidinedione compounds and oxadiazolidinedione compounds. These compounds are disclosed in WO 94/01433 (=Japanese Patent Application (Kokai) No. Hei 6-80667; Japanese Patent Application (Kokai) No. Hei 4-69383; WO 92/02520 (=Japanese Patent Application (Kohyo) No. Hei 6-500538); WO 91/07107 (=Japanese Patent Application (Kokai) No. Hei 3-170478=Japanese Patent Publication (Kokoku) No. Hei 7-8862); U.S. Pat. No. 5,132,317 (=Japanese Patent Application (Kokai) No. Hei 3-90071); U.S. Pat. No. 4,897,405 (=Japanese Patent Application (Kokai) No. Hei 2-292272); WO 89/08651 (=Japanese Patent Application (Kokai) No. Hei 1-272574); U.S. Pat. Nos. 5,061,717, 5,120,754, 5,223,522 (=Japanese Patent Application (Kokai) No. Hei 1-272573); U.S. Pat. Nos. 5,002,953, 5,194,443, 5,232,925, 5,260,445 (=Japanese Patent Application (Kokai) No. Hei 1-131169); U.S. Pat. No. 4,918,091 (Japanese Patent Application (Kokai) No. Sho 64-13076); U.S. Pat. Nos. 4,897,393, 4,948,900 (=Japanese Patent Application (Kokai) No. Sho 64-56675=Japanese Patent Publication (Kokoku) No. Hei 5-5832); U.S. Pat. No. 4,873,255 (=Japanese Patent Application (Kokai) No. Sho 64-38090); U.S. Pat. No. 4,703,052 (=Japanese Patent Application (Kokai) No. Sho 61-271287=Japanese Patent Publication (Kokoku) No. Hei 5-86953); U.S. Pat. No. 4,687,777 (=Japanese Patent Application (Kokai) No. Sho 61-267580=Japanese Patent Publication (Kokoku) No. Hei 5-31079); U.S. Pat. No. 4,725,610 (=Japanese Patent Application (Kokai) No. Sho 61-85372=Japanese Patent Publication (Kokoku) No. Hei 5-66956); U.S. Pat. No. 4,572,912 (=Japanese Patent Application (Kokai) No. Sho 60-51189=Japanese Patent Publication (Kokoku) No. Hei 2-31079); U.S. Pat. No. 4,461,902 (Japanese Patent Application (Kokai) No. Sho 58-118577=Japanese Patent Publication (Kokoku) No. Hei 2-57546); U.S. Pat. Nos. 4,287,200, 4,340,605, 4,438,141, 4,444,779 (=Japanese Patent Application (Kokai) No. Sho 55-22636=Japanese Patent Publication (Kokoku) No. Sho 62-42903); EP 0708098A (=Japanese Patent Application (Kokai) No. Hei 9-48779); EP 0676398A (=Japanese Patent Application (Kokai) No. Hei 7-330728); WO 95/18125; EP 0745600A; EP 0332332A (=Japanese Patent Application (Kokai) No. Hei 1-272574)

and EP 0604983A (=Japanese Patent Application (Kokai) No. Hei 6-247945), etc. Furthermore, the equal sign "=" indicates the corresponding patent or patents.

For example, 5-[4-(6-hydroxy-2,5,7,8-tetramethylchroman-2-ylmethoxy)benzyl]thiazolidine-2,4-dione (referred to as "troglitazone") is a thiazolidine derivative having activity that enhances insulin effects, and is known as an agent for the prevention and/or treatment of diabetes [Fujiwara, et al., Diabetes, Vol. 37, p. 1459 (1988); Hofmann, C. A. et al., Diabetes Care, Vol. 15, p. 1075 (1992)]. Moreover, since said compound has antioxidation effects, it is also reported to be useful as a therapeutic drug for insulin-dependent diabetes mellitus (type I diabetes: IDDM) [Tounyoubyou, Vol. 37, No. 2, pp. 127–129 (1994)].

However, there are no reports that troglitazone inhibits tissue invasion of lymphocytes, and that it is useful as a preventive and/or therapeutic agent of autoimmune diseases with the exception of insulin-dependent diabetes mellitus (type I diabetes). At present, insulin-dependent diabetes mellitus (type I diabetes) is considered to be a type of autoimmune disease. Although there is only one report indicating that troglitazone is useful for the treatment of insulin-dependent diabetes mellitus, this states the finding that troglitazone is useful for treatment or prevention of insulin-dependent diabetes mellitus is based on the antioxidation effects possessed by said compound. Thus, these known facts do not instruct or suggest that troglitazone inhibits tissue invasion of lymphocytes or that it is useful as a preventive and/or therapeutic agent for autoimmune diseases (excluding type I diabetes). Moreover, although it is known that other substances that improve insulin resistance are useful for treatment and prevention of diabetes, it is not known that these compounds inhibit tissue invasion of lymphocytes.

SUMMARY OF THE INVENTION

As a result of conducting earnest research on the pharmacological activity of substances that improve insulin resistance, the present inventors found that said substances inhibit invasion of lymphocytes into pancreatic β cells. From this it was also found that said substances are useful as preventive or therapeutic agents (preferably therapeutic agents) for autoimmune diseases (excluding type I diabetes), and accomplished the present invention.

The present invention provides a method for preventing and for treating autoimmune diseases (excluding type I diabetes) including, for example, diseases classified as systemic autoimmune diseases such as systemic lupus erythematosus, chronic rheumatoid arthritis, juvenile rheumatoid arthritis, Sjögren's syndrome, systemic scleriasis, mixed connective tissue disease and dermatomyositis; and, diseases classified as organ-specific autoimmune diseases such as Hashimoto's disease, primary myxedema, thyrotoxia, pernicious anemia, ulcerative colitis, autoimmune atrophic gastritis, idiopathic Addison's disease, male infertility, Goodpasture's syndrome, acute progressive glomerular nephritis, myasthenia gravis, multiple myositis, pemphigus vulgaris, bullous pemphigoid, sympathetic ophthalmia, multiple sclerosis, autoimmune hemolytic anemia, idiopathic thrombocytopenic purpura, postmyocardial infarction syndrome, rheumatic fever, lupoid hepatitis, primary biliary cirrhosis, Behcet's syndrome and Crest's syndrome.

The present invention provides compositions for the treatment or prevention of autoimmune diseases (excluding type I diabetes) containing as their active ingredient a substance that improves insulin resistance, their use for the preparation of pharmaceuticals for treatment or prevention of autoimmune diseases (excluding type I diabetes), or a treatment method or prevention method for autoimmune diseases (excluding type I diabetes) by administering pharmacologically effective amounts thereof to warm-blooded animals.

In the method of the present invention, the active ingredient substances that improve insulin resistance include thiazolidinedione compounds, oxazolidinedione compounds, isoxazolidinedione compounds and oxadiazolidinedione compounds, and preferably thiazolidinedione compounds. Furthermore, pharmacologically acceptable salts of thiazolidinedione compounds, etc. are included in the above-mentioned thiazolidinedione compounds and so forth.

DETAILED DESCRIPTION OF THE INVENTION

Figure 1:
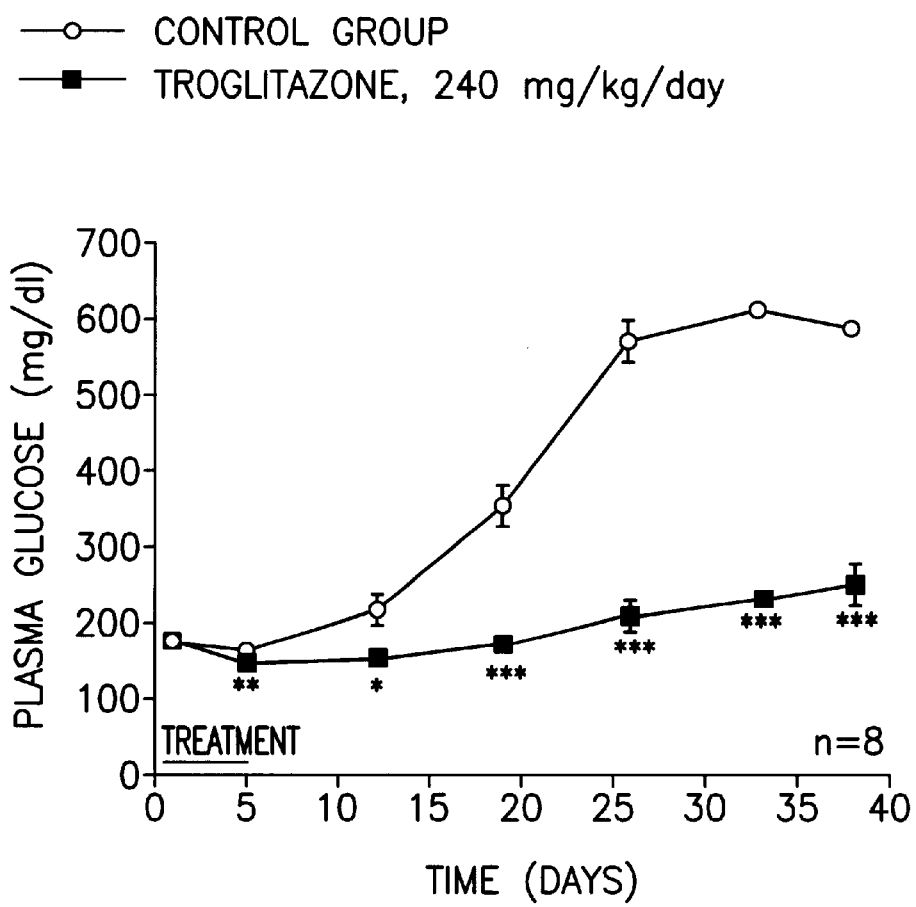
FIG. 1 is a graph plotting plasma glucose levels against time in a test for inhibiting effect on lymphocyte invasion.

The insulin resistance improving substances include, for example, the following compounds.

(I) In Japanese Patent Application (Kokai) No. Sho 60-51189 [Japanese Patent Publication (Kokoku) No. Hei 2-31079], U.S. Pat. No. 4,572,912 and European Patent No. 139421A, there is disclosed (1) a thiazolidine derivative of formula (I)

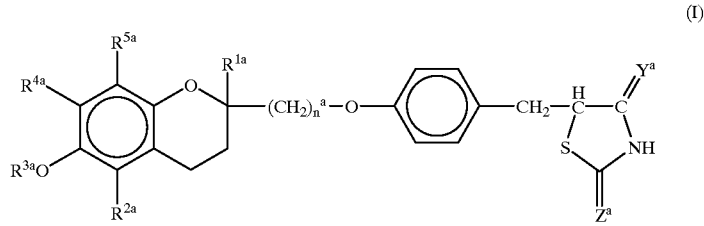

[wherein $R^{1a}$ and $R^{2a}$ may be the same or different and each represents a hydrogen atom or a $C_1$–$C_5$ alkyl group, $R^{3a}$ represents a hydrogen atom, a $C_1$–$C_6$ aliphatic acyl group, a $C_6$–$C_8$ cycloalkylcarbonyl group, a benzoyl or naphthoyl group which may have a substituent (the substituent is a $C_1$–$C_4$ alkyl, $C_1$–$C_4$ alkoxy, or hydroxy group, a halogen atom, or an amino, mono-$C_1$–$C_4$ alkylamino, di-$C_1$–$C_4$ alkylamino or a nitro group), a 4- to 7-membered heterocyclic acyl group containing from 1 to 3 hetero atoms selected from the hetero atom group consisting of nitrogen, oxygen and sulfur atoms, a phenylacetyl group, a phenylpropionyl group, a phenylacetyl or phenylpropionyl group substituted with at least one halogen atom, a cinnamoyl group, a $C_2$–$C_7$ alkoxycarbonyl group or a benzyloxycarbonyl group, $R^{4a}$ and $R^{5a}$ may be the same or different and each represents a hydrogen atom, a $C_1$–$C_5$ alkyl group or a $C_1$–$C_5$ alkoxy group, or $R^{4a}$ and $R^{5a}$ taken together represent a $C_1$–$C_4$ alkylenedioxy group, $Y^a$ and $Z^a$ may be the same or different and each represents an oxygen atom or an imino group, and $n^a$ is an integer of 1 to 3]

or a pharmacologically acceptable salt thereof.

In the compounds of formula (I), the details of definition of $R^{1a}$, $R^{2a}$, $R^{3a}$, $R^{4a}$, $R^{5a}$, $Y^a$, $Z^a$ and $n^a$, the kind of the pharmacologically acceptable salts, the process for preparation of the compounds of the formula (I), examples of the compounds, Examples, etc. are described in the above-mentioned publications.

Of which compounds of formula (I), preferable compounds are shown below:

(2) those in which $R^{1a}$ is a $C_1$–$C_4$ alkyl group, (3) those in which $R^{2a}$ is a hydrogen atom or a $C_1$–$C_3$ alkyl group, (4) those in which $R^{3a}$ is a hydrogen atom, a $C_1$–$C_4$ aliphatic acyl group, an unsubstituted benzoyl or naphthoyl group or a $C_2$–$C_4$ alkoxycarbonyl group, (5) those in which $R^{4a}$ is a $C_1$–$C_4$ alkyl group, (6) those in which $R^{5a}$ is a hydrogen atom or a $C_1$–$C_3$ alkyl group, (7) those in which $R^{1a}$ is a $C_1$–$C_4$ alkyl group, $R^{2a}$ is a hydrogen atom or a $C_1$–$C_3$ alkyl group, $R^{3a}$ is a hydrogen atom, a $C_1$–$C_4$ aliphatic acyl group, an unsubstituted benzoyl or naphthoyl group or a $C_2$–$C_4$ alkoxycarbonyl group, $R^{4a}$ is a $C_1$–$C_4$ alkyl group, and $R^{5a}$ is a hydrogen atom or a $C_1$–$C_3$ alkyl group, (8) those in which $R^{3a}$ is a hydrogen atom, or an acetyl, benzoyl or ethoxycarbonyl group, (9) those in which $R^{1a}$ is a $C_1$–$C_4$ alkyl group, $R^{2a}$ is a hydrogen atom or a $C_1$–$C_3$ alkyl group, $R^{3a}$ is a hydrogen atom, or an acetyl, benzoyl or ethoxycarbonyl group, $R^{4a}$ is a $C_1$–$C_4$ alkyl group, and $R^{5a}$ is a hydrogen atom or a $C_1$–$C_3$ alkyl group,

(10) those in which $R^{1a}$ is a methyl group,

(11) those in which $R^{2a}$ is a hydrogen atom or a methyl group,

(12) those in which $R^{3a}$ is a hydrogen atom, or an acetyl or ethoxycarbonyl group,

(13) those in which $R^{4a}$ is a methyl or t-butyl group,

(14) those in which $R^{5a}$ is a hydrogen atom or a methyl group,

(15) those in which $R^{1a}$ is a methyl group, $R^{2a}$ is a hydrogen atom or a methyl group, $R^{3a}$ is a hydrogen atom, or an acetyl or ethoxycarbonyl group, $R^{4a}$ is a methyl or t-butyl group, and $R^{5a}$ is a hydrogen atom or a methyl group,

(16) those selected from i) 5-[4-(6-hydroxy-2,5,7,8-tetramethylchroman-2-ylmethoxy)benzyl]thiazolidine-2,4-dione (troglitazone), ii) 5-[4-(6-hydroxy-2-methyl-7-t-butylchroman-2-ylmethoxy)benzyl]thiazolidine-2,4-dione, iii) 5-[4-(6-hydroxy-2-ethyl-5,7,8-trimethylchroman-2-ylmethoxy)benzyl]thiazolidine-2,4-dione, iv) 5-[4-(6-hydroxy-2-isobutyl-5,7,8-trimethylchroman-2-ylmethoxy)benzyl]thiazolidine-2,4-dione, v) 5-[4-(6-acetoxy-2,5,7,8-tetramethylchroman-2-ylmethoxy)benzyl]thiazolidine-2,4-dione, and vi) 5-[4-(6-ethoxycarbonyloxy-2,5,7,8-tetramethylchroman-2-ylmethoxy)-benzyl]thiazolidine-2,4-dione.

(II) In Japanese Patent Application (Kokai) No. Sho 61-267580 [Japanese Patent Publication (Kokoku) No. Hei 5-66956] and U.S. Pat. No. 4,687,777, there is disclosed (1) a thiazolidine derivative of the formula (II):

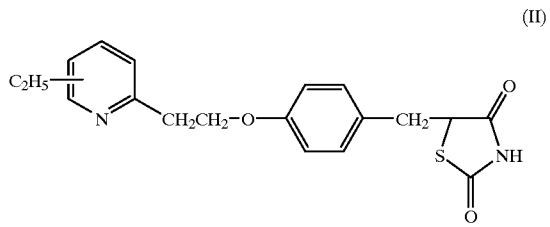

or a pharmacologically acceptable salt thereof.

The details of the kind of the pharmacologically acceptable salts, the process for preparation, examples of the compounds, Examples, etc. of the compound of the formula (II) are described in the above-mentioned publications.

Of which compounds of formula (II), preferable compounds are shown below:

(2) a compound selected from i) 5-{4-[2-(3-ethyl-2-pyridyl)ethoxy]benzyl}-2,4-thiazolidinedione, ii) 5-{4-[2-(4-ethyl-2-pyridyl)ethoxy]benzyl}-2,4-thiazolidinedione, iii) 5-{4-[2-(5-ethyl-2-pyridyl)ethoxy]benzyl}-2,4-thiazolidinedione (hereinafter referred to as "pioglitazone"), and iv) 5-{4-[2-(6-ethyl-2-pyridyl)ethoxy]benzyl}-2,4-thiazolidinedione.

(III) In Japanese Patent Application (Kokai) No. Sho 61-271287 [Japanese Patent Publication (Kokoku) No. Hei 5-86953] and U.S. Pat. No. 4,703,052, there is described (1) a compound of the formula (III)

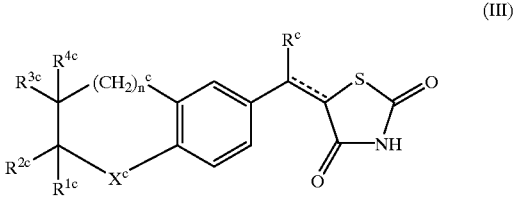

(III)

[wherein the broken line represents a single bond or a non-bond, $n^c$ is 0, 1 or 2, $X^c$ is O, S, S=O or S(=O)(=O), $R^c$ is H, $CH_3$ or $C_2H_5$, $R^{1c}$ is independently H, $C_5$–$C_7$ cycloalkyl, $C_6$–$C_8$ methylcycloalkyl, pyridyl, thienyl, furyl, naphthyl, p-biphenylyl, tetrahydrofuranyl, tetrahydrothienyl, tetrahydropyranyl, $C_6H_4W^{2c}$ [wherein $W^{2c}$ is H, OH, F, Cl, Br, $C_1$–$C_4$ alkyl, $C_1$–$C_4$ alkoxy or $C_1$–$C_4$ thioalkyl] or alk-$W^{1c}$ [wherein alk is $C_1$–$C_6$ alkylene, ethylidene or isopropylidene, $W^{1c}$ is H, OH, $C_1$–$C_4$ alkoxy, $C_1$–$C_4$ thioalkyl, pyridyl, furyl, thienyl, tetrahydrofuryl, tetrahydrothienyl, naphthyl, $C_5$–$C_7$ cycloalkyl or $C_6H_4W^{2c}$], $R^{2c}$ is H or $CH_3$, $R^{3c}$ is H, $C_1$–$C_6$ alkyl, $C_6H_4W^{2c}$ or benzyl, $R^{4c}$ is H, in the case where $R^{1c}$ and $R^{2c}$ are taken together, they form $C_4$–$C_6$ alkylene, $R^{3c}$ and $R^{4c}$ each are H, in the case where $R^{3c}$ and $R^{4c}$ are taken together, they form $C_4$–$C_6$ alkylene, $R^{1c}$ and $R^{2c}$ are H, in the case where $R^{2c}$ and $R^{3c}$ are taken together, they form $C_3$–$C_4$ alkylene, and $R^{1c}$ and $R^{4c}$ each are H], or a pharmacologically acceptable salt thereof.

In the compounds of formula (III), the details of definition of $R^{1c}$, $R^{2c}$, $R^{3c}$, $W^{1c}$, $W^{2c}$ and alk, the kind of the pharmacologically acceptable salts, the process for preparation of the compounds of the formula (III), Examples, etc. are described in the above-mentioned publications.

Of which the compounds of formula (III), preferable compounds are shown below:

(2) those described in (1) in which $R^c$ is H, the broken line is a non-bond, and $n^c$ is 0 or 1, (3) those described in (2) in which $R^{2c}$, $R^{3c}$ and $R^{4c}$ each are H, $R^{1c}$ is H, cyclohexyl, $C_6H_4W^{2c}$ (wherein $W^{2c}$ is H, F, Cl, Br, $CH_3$ or $CH_3O$) or alk-$W^{1c}$ [wherein alk is $C_1$–$C_4$ alkylene, ethylidene or isopropylidene, and $W^{1c}$ is H, OH, $C_1$–$C_4$ alkoxy, cyclohexyl or $C_6H_4W^{2c}$], (4) those described in (3) in which $X^c$ is O, $R^{1c}$ is cyclohexyl, cyclohexylmethyl, benzyl, fluorobenzyl, $C_1$–$C_4$ alkyl, hydroxymethyl, methoxymethyl or ethoxyethyl, (5) those described in (4) in which $R^{1c}$ is benzyl, (6) those described in (5) which are 5-[(2-benzyl-2,3-dihydrobenzofuran-5-yl)methyl]thiazolidine-2,4-dione, 5-[(2-benzyl-3,4-dihydro-2H-benzopyran-6-yl)methyl] thiazolidine-2,4-dione (hereinafter referred to as "englitazone") or a sodium salt thereof, (7) those described in (2) in which $R^{2c}$ and $R^{3c}$ taken together form $(CH_2)_4$, $R^{1c}$ and $R^{4c}$ each are H, and $X^c$ is O, (8) (a) those described in (2) in which (a) $R^{1c}$ and $R^{2c}$ taken together form $(CH_2)_5$, $R^{3c}$ and $R^{4c}$ each are H and $X^c$ is O, or (b) $R^{3c}$ and $R^{4c}$ taken together form $(CH_2)_5$, $R^{1c}$ and $R^{2c}$ each are H and $X^c$ is O, and (9) those described in (3) in which $n^c$ is 0, $R^{1c}$ is H, $CH_3$ or benzyl, and $X^c$ is S or S(=O)(=O).

(IV) In Japanese Patent Application (Kokai) No. Hei 1-131169, U.S. Pat. Nos. 5,002,953, 5,194,443, 5,232,925 and 5,260,445, there is disclosed (1) a compound of formula (IV):

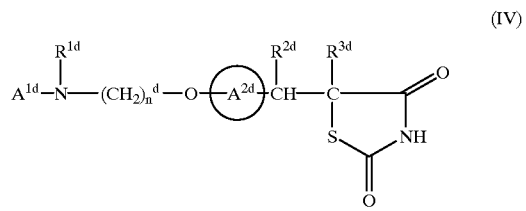

(IV)

[wherein $A^{1d}$ represents an optionally substituted aromatic heterocyclic group, $R^{1d}$ represents a hydrogen atom, an alkyl group, an acyl group an aralkyl group (wherein the aryl moiety may be substituted or unsubstituted) or an optionally substituted aryl group, $R^{2d}$ and $R^{3d}$ each represent hydrogen or $R^{2d}$ and $R^{3d}$ taken together form a bond;

$A^{2d}$ represents a benzene ring having not more than 5 substituents in total; and $n^d$ is an integer of 2 to 6]

or a pharmaceutically acceptable salt thereof.

In the compound of formula (IV), the details of definition of $A^{1d}$, $R^{1d}$, $R^{2d}$, $R^{3d}$, $A^{2d}$ and $n^d$, the kind of the pharmaceutically acceptable salts, the process for preparation of the compound of formula (IV), Examples thereof, the preferable compounds, etc. are described in the above-mentioned publications.

Of which compounds of formula (IV), preferable compounds are shown below:

(2) those described in (1) in which $A^{1d}$ represents an optionally substituted aromatic heterocyclic group of a single ring or a condensed ring containing 4 or less hetero atoms selected from oxygen, sulfur and nitrogen, (3) those described in (1) or (2) in which $A^{1d}$ represents a moiety of the formula (a), (b) or (c):

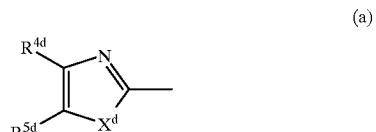

(a)

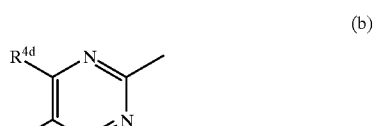

(b)

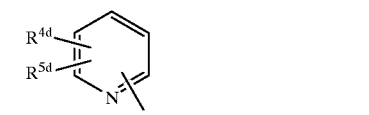

(c)

[wherein $R^{4d}$ and $R^{5d}$ each independently represent a hydrogen atom, an alkyl group or an optionally substituted aryl group, or in the case where $R^{4d}$ and $R^{5d}$ are each bonded to a carbon atom, they may together form a benzene ring with the carbon atoms to which they are attached, and additionally each carbon atom bonded to $R^{4d}$ and $R^{5d}$ may be substituted or unsubstituted; and $X^d$ in the moiety of the formula (a) represents oxygen or sulfur], (4) those described in (3) in which $R^{4d}$ and $R^{5d}$ each independently represent hydrogen, alkyl or an optionally substituted phenyl group,
(5) those described in (3) in which $R^{4d}$ and $R^{5d}$ taken together represent a moiety of formula (d):

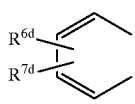

(d)

(wherein $R^{6d}$ and $R^{7d}$ each independently represent hydrogen, halogen, optionally substituted alkyl or alkoxy),
(6) those described in (5) in which $R^{6d}$ and $R^{7d}$ both represent hydrogen,
(7) those described in any one of (1) to (6) in which $A^{2d}$ represents a moiety of formula (e):

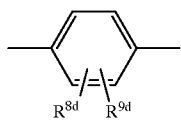

(e)

(wherein $R^{8d}$ and $R^{9d}$ each independently represent hydrogen, halogen, optionally substituted alkyl or alkoxy),
(8) those described in (7) in which $R^{8d}$ and $R^{9d}$ each represent hydrogen,
(9) those described in (1) of the formula (f):

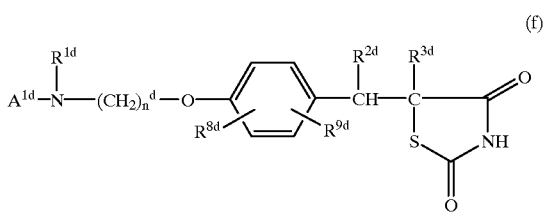

(f)

[wherein $A^{1d}$, $R^{1d}$, $R^{2d}$, $R^{3d}$ and $n^d$ have the same meanings as defined for the formula (IV) of (1), and $R^{8d}$ and $R^{9d}$ have the same meanings as defined for the formula (e) of (7)] or a pharmacologically acceptable salt thereof,
(10) those described in any one of (1) to (9) in which $n^d$ is an integer of 2 or 3,
(11) those described in any one of (1) to (10) in which $R^{1d}$ represents a methyl group,
(12) those described in (1) selected from
  i) 5-{4-[2-(N-methyl-N-(2-benzothiazolyl)amino)ethoxy]benzyl}thiazolidine-2,4-dione,
  ii) 5-{4-[2-(N-methyl-N-(2-pyrimidinyl)amino)ethoxy]benzyl}thiazolidine-2,4-dione,
  iii) 5-{4-[2-(N-methyl-N-(2-[4,5-dimethylthiazolyl)]amino)ethoxy]benzyl}thiazolidine-2,4-dione,
  iv) 5-{4-[2-(N-methyl-N-(2-thiazolyl)amino)ethoxy]benzyl}thiazolidine-2,4-dione,
  v) 5-{4-[2-(N-methyl-N-(2-[4-phenylthiazolyl])amino)ethoxy]benzyl}thiazolidine-2,4-dione,
  vi) 5-{4-[2-(N-methyl-N-(2-[4-phenyl-5-methylthiazolyl])amino)ethoxy]benzyl}thiazolidine-2,4-dione,
  vii) 5-{4-[2-(N-methyl-N-(2-[4-methyl-5-phenylthiazolyl])amino)ethoxy]benzyl}thiazolidine-2,4-dione,
  viii) 5-{4-[2-(N-methyl-N-(2-[5-phenyloxazolyl])amino)ethoxy]benzyl}thiazolidine-2,4-dione,
  ix) 5-{4-[2-(N-methyl-N-(2-[4,5-dimethyloxazolyl])amino)ethoxy]benzyl}thiazolidine-2,4-dione,
  x) 5-{4-[2-(2-pyrimidinylamino)ethoxy]benzyl}thiazolidine-2,4-dione,
  xi) 5-{4-[2-(N-acetyl-N-(2-pyrimidinyl)amino)ethoxy]benzyl}thiazolidine-2,4-dione,
  xii) 5-{4-[2-(N-(2-benzothiazolyl)-N-benzylamino)ethoxy]benzyl}thiazolidine-2,4-dione,
  xiii) 5-{4-[3-(N-methyl-N-(2-benzoxazolyl)amino)propoxy]benzyl}thiazolidine-2,4-dione, and
  xiv) 5-{4-[2-(N-methyl-N-(2-pyridyl)amino)ethoxy]benzyl}thiazolidine-2,4-dione (hereinafter referred to as "BRL-49653"),
(13) those described in (1) which is 5-{4-[2-(N-methyl-N-(2-pyridyl)amino)ethoxy]benzyl}thiazolidine-2,4-dione (BRL-49653).

In the above-mentioned (2) to (11), the details of the definition of $R^{4d}$, $R^{5d}$, $R^{6d}$, $R^{7d}$, $R^{8d}$ and $R^{9d}$ are described in the above-mentioned publications.

(V) In Japanese Patent Application (Kokai) No. Hei 9-48779 and European Patent No. 708098A, there is described
(1) an oxime derivative of the formula (V):

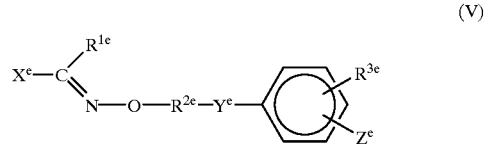

(V)

[wherein
$R^{1e}$ represents a hydrogen atom or a straight or branched chain alkyl group having from 1 to 6 carbon atoms,
$R^{2e}$ represents a straight or branched chain alkylene group having from 2 to 6 carbon atoms,
$R^{3e}$ represents a hydrogen atom, a straight or branched chain alkyl group having from 1 to 6 carbon atoms, a straight or branched chain alkoxy group having from 1 to 4 carbon atoms, a straight or branched chain alkylthio group having from 1 to 4 carbon atoms, a halogen atom, a nitro group, an amino group, a straight or branched chain mono-alkylamino group having from 1 to 4 carbon atoms, a straight or branched chain dialkylamino group in which the alkyls may be the same or different and each has from 1 to 4 carbon atoms, an aryl group having from 6 to 10 carbon atoms or an aralkyl group having from 7 to 12 carbon atoms,
$X^e$ represents an aryl group having from 6 to 10 carbon atoms which may have from 1 to 3 substituents α or an aromatic heterocyclic group which may have from 1 to 3 substituents α.

The substituent α represents (i) a straight or branched chain alkyl group having from 1 to 6 carbon atoms, (ii) a straight or branched chain halogenoalkyl group having from 1 to 4 carbon atoms, (iii) a hydroxy group, (iv) a straight or branched chain acyloxy group having from 1 to 4 carbon atoms, (v) a straight or branched chain alkoxy group having from 1 to 4 carbon atoms, (vi) a straight or branched chain alkylenedioxy group having from 1 to 4 carbon atoms, (vii) an aralkyloxy group having from 7 to 12 carbon atoms, (viii) a straight or branched chain alkylthio group having from 1 to 4 carbon atoms, (ix) a straight or branched chain alkylsulfonyl group having from 1 to 4 carbon atoms, (x) a halogen atom, (xi) a nitro group, (xii) an amino group, (xiii) a straight or branched chain mono-alkylamino group having from 1 to 4 carbon atoms, (xiv) a straight or branched chain dialkylamino group in which the alkyls may be the same or different and each has from 1 to 4 carbon atoms, (xv) an aralkyl group having from 7 to 12 carbon atoms, (xvi) an aryl group having from 6 to 10 carbon atoms which may have a substituent β, (xvii) an aryloxy group having from 6 to 10 carbon atoms which may have a substituent β, (xviii) an arylthio group having from 6 to 10 carbon atoms which may have a substituent β, (xix) an arylsulfonyl group having from 6 to 10 carbon atoms which may have a substituents β, (xx) an arylsulfonylamino group having from 6 to 10 carbon atoms which may have a substituents β (the nitrogen atom of the amino moiety may be substituted with a straight or branched chain alkyl group having from 1 to 6 carbon atoms), (xxi) an aromatic heterocyclic group, (xxii) an aromatic heterocyclyloxy group, (xxiii) an aromatic heterocyclylthio group, (xxiv) an aromatic heterocyclysulfonyl group, or (xxv) an aromatic heterocyclysulfonylamino group (the nitrogen atom of the amino moiety may be substituted with a straight or branched chain alkyl group having from 1 to 6 carbon atoms).

The substituents β represents a straight or branched chain alkyl group having from 1 to 6 carbon atoms, a straight or branched chain halogenoalkyl group having from 1 to 4 carbon atoms, a straight or branched chain alkoxy group having from 1 to 4 carbon atoms, a halogen atom or straight or branched chain alkylenedioxy group having from 1 to 4 carbon atoms, $Y^e$ represents an oxygen atom, a sulfur atom or a group of formula >N—$R^{4e}$ (wherein $R^{4e}$ represents a hydrogen atom, a straight or branched chain alkyl group having from 1 to 6 carbon atoms or a straight or branched chain acyl group having from 1 to 8 carbon atoms), and $Z^e$ represents a 2,4-dioxothiazolidin-5-ylidenylmethyl group, a 2,4-dioxothiazolidin-5-ylmethyl group, a 2,4-dioxooxazolidin-5-ylmethyl group or a 3,5-dioxooxadiazolidin-2-ylmethyl group]

or a pharmacologically acceptable salt thereof.

In the compounds of formula (V), the details of the definition of $R^{1e}$, $R^{2e}$, $R^{3e}$, $R^{4e}$, α, β, $X^e$, $Y^e$ and $Z^e$, the kind of the pharmacologically acceptable salt, the process for preparation of the compound of formula (V), examples of the compounds, Examples, etc. are described in the above-mentioned publications.

Of which compound of formula (V), preferred compounds are shown below:

(2) those described in (1) in which $R^{1e}$ represents a hydrogen atom or a straight or branched chain alkyl group having from 1 to 4 carbon atoms, (3) those described in (1) in which $R^{1e}$ represents a hydrogen atom or a straight or branched chain alkyl group having from 1 to 3 carbon atoms, (4) those described in (1) in which $R^{1e}$ represents a hydrogen atom, a methyl or ethyl group, (5) those described in (1) in which $R^{1e}$ represents a methyl or ethyl group, (6) those described in (1) in which $R^{2e}$ represents a straight or branched chain alkylene group having from 2 to 5 carbon atoms, (7) those described in (1) in which $R^{2e}$ represents a straight or branched chain alkylene group having 2 or 3 carbon atoms, (8) those described in (1) in which $R^{2e}$ represents an ethylene, trimethylene or methylethylene group, (9) those described in (1) in which $R^{2e}$ represents an ethylene group,

(10) those described in (1) in which $R^{3e}$ represents a hydrogen atom, a straight or branched chain alkyl group having from 1 to 4 carbon atoms, an alkoxy group having 1 or 2 carbon atoms, an alkylthio group having 1 or 2 carbon atoms or a halogen atom,

(11) those described in (1) in which $R^{3e}$ represents a hydrogen atom,

(12) those described in (1) in which $X^e$ represents an aryl group having from 6 to 10 carbon atoms which may have from 1 to 3 substituents α or a 5- to 10-membered aromatic heterocyclic group (comprising one or two rings) having from 1 to 3 nitrogen, oxygen and/or sulfur atoms which may have from 1 to 3 substituents α.

The substituent α represents (i) a straight or branched chain alkyl having from 1 to 6 carbon atoms, (ii) a straight or branched chain halogenoalkyl having from 1 to 4 carbon atoms, (iii) a hydroxy group, (iv) a straight or branched chain acyloxy group having from 1 to 4 carbon atoms, (v) a straight or branched chain alkoxy group having from 1 to 4 carbon atoms, (vi) a straight or branched chain alkylenedioxy group having from 1 to 4 carbon atoms, (vii) an aralkyloxy group having from 7 to 12 carbon atoms, (viii) a straight or branched chain alkylthio group having from 1 to 4 carbon atoms, (ix) a straight or branched chain alkylsulfonyl group having from 1 to 4 carbon atoms, (x) a halogen atom, (xi) an aralkyl group having from 7 to 12 carbon atoms, (xii) a phenyl group which may have a substituent β, (xiii) a phenoxy group which may have a substituent β, (xiv) a phenylthio group which may have a substituent β, (xv) a phenylsulfonyl group which may have a substituent β, (xvi) a phenylsulfonylamino group which may have a substituent β (the nitrogen atom of the amino moiety may be substituted with a straight or branched chain alkyl group having from 1 to 6 carbon atoms), (xvii) a furyl, thienyl, oxazolyl, isoxazolyl, thiazolyl, pyridyl, pyridyloxy, pyridylthio or pyridylsulfonyl group, (xviii) an imidazolyl group (the nitrogen atom may be substituted with a straight or branched chain alkyl group having from 1 to 6 carbon atoms), and/or (xix) a pyridylsulfonylamino group (the nitrogen atom of the amino moiety may be substituted with a straight or branched chain alkyl group having from 1 to 6 carbon atoms).

The substituent β represents a straight or branched chain alkyl group having from 1 to 6 carbon atoms, a straight or branched chain halogenoalkyl group having from 1 to 4 carbon atoms, a straight or branched chain alkoxy group having from 1 to 4 carbon atoms, a halogen atom or a straight or branched chain alkylenedioxy group having from 1 to 4 carbon atoms,

(13) those described in (1) in which $X^e$ represents an aryl group having from 6 to 10 carbon atoms which may have from 1 to 3 substituent α or a 5- to 10-membered aromatic heterocyclic group (comprising one or two rings) having from 1 to 3 nitrogen, oxygen and/or sulfur atoms which may have from 1 to 3 substituents α.

The substituent α represents (i) a straight or branched chain alkyl group having from 1 to 6 carbon atoms, (ii) a straight or branched chain halogenoalkyl group having from 1 to 4 carbon atoms, (iii) a hydroxy group, (iv) a straight or branched chain alkanoyloxy group having from 1 to 4 carbon atoms, (v) a straight or branched chain alkoxy group having from 1 to 4 carbon atoms, (vi) a straight or branched chain alkylenedioxy group having from 1 to 4 carbon atoms, (vii) an aralkyloxy group having from 7 to 12 carbon atoms, (viii) a straight or branched chain alkylthio group having from 1 to 4 carbon atoms, (ix) a straight or branched chain alkylsulfonyl group having from 1 to 4 carbon atoms, (x) fluorine, chlorine or bromine atoms, (xi) an aralkyl group having from 7 to 12 carbon atoms, (xii) a phenyl group which may have a substituent β, (xiii) a phenoxy group which may have a substituent β, (xiv) a phenylthio group which may have a substituent β, (xv) a phenylsulfonyl group which may have a substituent β, (xvi) a phenylsulfonylamino group which may have a substituent β (the nitrogen atom of the amino moiety may be substituted with a straight or branched chain alkyl group having from 1 to 6 carbon atoms), (xvii) a furyl, thienyl, oxazolyl, isoxazolyl, thiazolyl, pyridyl, pyridyloxy, pyridylthio or pyridylsulfonyl group, (xviii) an imidazolyl group (the nitrogen atom may be substituted with a straight or branched chain alkyl group having from 1 to 6 carbon atoms), and/or (xix) a pyridylsulfonylamino group (the nitrogen atom of the amino moiety may be substituted with a straight or branched chain alkyl group having from 1 to 6 carbon atoms).

The substituents β represents a straight or branched chain alkyl group having from 1 to 6 carbon atoms, a straight or branched chain halogenoalkyl group having from 1 to 4 carbon atoms, a straight or branched chain alkoxy group having from 1 to 4 carbon atoms, a halogen atom or a straight or branched chain alkylenedioxy group having from 1 to 4 carbon atoms,

(14) those described in (1) in which $X^e$ represents a phenyl, naphthyl, imidazolyl, oxazolyl, pyridyl, indolyl, quinolyl or isoquinolyl group, and these groups optionally having 1 to 3 substituents α.

The substituent α represents (i) a straight or branched chain alkyl group having from 1 to 6 carbon atoms, (ii) a straight or branched chain halogenoalkyl group having from 1 to 4 carbon atoms, (iii) a hydroxy group, (iv) a straight or branched chain alkanoyloxy group having from 1 to 4 carbon atoms, (v) a straight or branched chain alkoxy group having from 1 to 4 carbon atoms, (vi) a methylenedioxy group, (vii) an aralkyloxy group having from 7 to 12 carbon atoms, (viii) a straight or branched chain alkylthio group having from 1 to 4 carbon atoms, (ix) a straight or branched chain alkylsulfonyl group having from 1 to 4 carbon atoms, (x) a fluorine, chlorine or bromine atom, (xi) an aralkyl group having from 7 to 12 carbon atoms, (xii) a phenyl group (the phenyl group may be substituted with methyl, trifluoromethyl, methoxy, fluoro or methylenedioxy), (xiii) a phenoxy group (the phenyl group may be substituted with methyl, trifluoromethyl, methoxy, fluoro or methylenedioxy), (xiv) a phenylthio group (the phenyl group may be substituted with methyl, trifluoromethyl, methoxy, fluoro or methylenedioxy), (xv) a phenylsulfonyl group (the phenyl group may be substituted with methyl, trifluoromethyl, methoxy, fluoro or methylenedioxy), (xvi) a phenylsulfonylamino group (the phenyl group may be substituted with methyl, trifluoromethyl, methoxy, fluoro or methylenedioxy, and the nitrogen atom of the amino moiety may be substituted with a straight or branched chain alkyl group having from 1 to 6 carbon atoms), (xvii) furyl, thienyl, oxazolyl, isoxazolyl, thiazolyl, pyridyl, pyridyloxy, pyridylthio or pyridylsulfonyl group, (xviii) an imidazolyl group (the nitrogen atom may be substituted with a straight or branched chain alkyl group having from 1 to 6 carbon atoms), and/or (xix) a pyridylsulfonylamino group (the nitrogen atom of the amino moiety may be substituted with a straight or branched chain alkyl group having from 1 to 6 carbon atoms),

(15) those described in (1) in which $X^e$ represents a phenyl, naphthyl, imidazolyl, oxazolyl, pyridyl, indolyl, quinolyl or isoquinolyl group, and these groups optionally having from 1 to 3 substituents α.

The substituent α represents (i) a straight or branched chain alkyl group having from 1 to 6 carbon atoms, (ii) a straight or branched chain halogenoalkyl group having from 1 to 4 carbon atoms, (iii) a hydroxy group, (iv) a straight or branched chain alkanoyloxy group having from 1 to 4 carbon atoms, (v) a straight or branched chain alkoxy group having from 1 to 4 carbon atoms, (vi) a methylenedioxy, benzyloxy, phenethyloxy or naphthylmethoxy group, (vii) a straight or branched chain alkylthio group having from 1 to 4 carbon atoms, (viii) a straight or branched chain alkylsulfonyl group having from 1 to 4 carbon atoms, (ix) a fluorine, chlorine or bromine atom, (x) a benzyl group, (xi) a phenyl group (the phenyl group may be substituted with methyl, trifluoromethyl, methoxy, fluoro or methylenedioxy), (xii) a phenoxy group (the phenyl group may be substituted with methyl, trifluoromethyl, methoxy, fluoro or methylenedioxy), (xiii) a phenylthio, phenylsulfonyl, phenylsulfonylamino, N-methylphenylsulfonylamino, furyl, thienyl, oxazolyl, isoxazolyl, thiazolyl, pyridyl, pyridyloxy, pyridylthio, pyridylsulfonyl, pyridylsulfonylamino or N-methylpyridylsulfonylamino group, and/or (xiv) an imidazolyl group (the nitrogen atom may be substituted with a straight or branched chain alkyl group having from 1 to 6 carbon atoms),

(16) those described in (1) in which $X^e$ represents a phenyl, naphthyl, pyridyl, indolyl, quinolyl or isoquinolyl group, and these groups optionally having from 1 to 3 substituents α.

The substituent α represents (i) a straight or branched chain alkyl group having from 1 to 3 carbon atoms, (ii) a trifluoromethyl, difluoromethyl, fluoromethyl, hydroxy, formyloxy or acetoxy group, (iii) a straight or branched chain alkoxy group having from 1 to 3 carbon atoms, (iv) a methylenedioxy, benzyloxy, methylthio, ethylthio, methylsulfonyl or ethylsulfonyl group, (v) a fluorine, chlorine or bromine atom, and (vi) a benzyl, phenyl, 4-methylphenyl, 4-trifluoromethylphenyl, 4-methoxyphenyl, 4-fluorophenyl, 3,4-methylenedioxyphenyl, phenoxy, phenylthio, phenylsulfonyl, phenylsulfonylamino, N-methylphenylsulfonylamino, furyl, thienyl, oxazolyl, thiazolyl, imidazolyl, N-methylimidazolyl, pyridyl, pyridyloxy, pyridylthio, pyridylsulfonyl, pyridylsulfonylamino and/or N-methylpyridylsulfonylamino group,

(17) those described in (1) in which $X^e$ represents a phenyl, naphthyl, pyridyl, quinolyl or isoquinolyl group, and these groups optionally having from 1 to 3 substituents α.

The substituent α represents a methyl, ethyl, isopropyl, trifluoromethyl, hydroxy, acetoxy, methoxy, ethoxy, isopropoxy, methylenedioxy, benzyloxy, methylthio, ethylthio, methylsulfonyl, ethylsulfonyl group, a chlorine atom, or a benzyl, phenyl, phenoxy, phenylthio, phenylsulfonyl, phenylsulfonylamino, N-methylphenylsulfonylamino, pyridyl, pyridyloxy, pyridylthio, pyridylsulfonyl, pyridylsulfonylamino and/or N-methylpyridylsulfonylamino group,

(18) those described in (1) in which $X^e$ represents a phenyl group which may have from 1 to 3 substituents α.

The substituent α represents a methyl, hydroxy or acetoxy group, a chlorine atom, or a benzyl, phenyl, phenoxy, phenylthio, phenylsulfonyl, phenylsulfonylamino, N-methylphenylsulfonylamino, pyridyl, pyridyloxy, pyridylthio and/or pyridylsulfonyl group,

(19) those described in (1) in which $X^e$ represents a pyridyl group which may have from 1 to 3 substituents α.

The substituent α represents a methoxy, ethoxy, isopropoxy, benzyloxy, methylthio, ethylthio, methylsulfonyl, ethylsulfonyl, benzyl, phenyl, phenoxy, phenylthio, phenylsulfonyl, phenylsulfonylamino and/or N-methylphenylsulfonylamino group,

(20) those described in (1) in which $Y^e$ represents an oxygen or sulfur atom or a group of formula >N—$R^{4e}$ (wherein $R^{4e}$ represents a hydrogen atom, a straight or branched chain alkyl group having from 1 to 3 carbon atoms or a straight or branched chain alkanoyl group having from 2 to 5 carbon atoms),

(21) those described in (1) in which $Y^e$ represents an oxygen atom,

(22) the compound described in (1) in which $Z^e$ represents an 2,4-dioxothiazolidin-5-ylmethyl group, a 2,4-dioxooxazolidin-5-ylmethyl group or a 3,5-dioxooxadiazolidin-2-ylmethyl group,

(23) those described in (1) in which $Z^e$ represents a 2,4-dioxothiazolidin-5-ylmethyl group or a 2,4-dioxooxazolidin-5-ylmethyl group,

(24) those described in (1) in which $Z^e$ represents a 2,4-dioxothiazolidin-5-ylmethyl group,

(25) those described in (1) in which $R^{1e}$ represents a hydrogen atom or a straight or branched chain alkyl group having from 1 to 4 carbon atoms;

$R^{2e}$ represents a straight or branched chain alkylene group having from 2 to 5 carbon atoms;

$R^{3e}$ represents a hydrogen atom, a straight or branched chain alkyl group having 1 or 4 carbon atoms, an alkoxy group having 1 or 2 carbon atoms, an alkylthio group having 1 or 2 carbon atoms or a halogen atom;

$X^e$ represents an aryl group having from 6 to 10 carbon atoms which may have from 1 to 3 substituents α, or a 5- to 10-membered aromatic heterocyclic group (comprising one or two rings) having from 1 to 3 nitrogen atoms, oxygen atoms and/or sulfur atoms which may have from 1 to 3 substituents α.

The substituent α represents (i) a straight or branched chain alkyl group having from 1 to 6 carbon atoms, (ii) a straight or branched chain halogenoalkyl group having from 1 to 4 carbon atoms, (iii) a hydroxy group, (iv) a straight or branched chain acyloxy group having from 1 to 4 carbon atoms, (v) a straight or branched chain alkoxy group having from 1 to 4 carbon atoms, (vi) a straight or branched chain alkylenedioxy group having from 1 to 4 carbon atoms, (vii) an aralkyloxy group having from 7 to 12 carbon atoms, (viii) a straight or branched chain alkylthio group having from 1 to 4 carbon atoms, (ix) a straight or branched chain alkylsulfonyl group having from 1 to 4 carbon atoms, (x) a halogen atom, (xi) an aralkyl group having from 7 to 12 carbon atoms, (xii) a phenyl group which may have a substituent β, (xiii) a phenoxy group which may have a substituent β, (xiv) a phenylthio group which may have a substituent β, (xv) a phenylsulfonyl group which may have a substituent β, (xvi) a phenylsulfonylamino group which may have a substituent β (the nitrogen atom of the amino moiety may be substituted with a straight or branched chain alkyl group having from 1 to 6 carbon atoms), (xvii) a furyl, thienyl, oxazolyl, isoxazolyl, thiazolyl, pyridyl, pyridyloxy, pyridylthio or pyridylsulfonyl group, (xviii) an imidazolyl group (the nitrogen atom may be substituted with straight a or branched chain alkyl group having from 1 to 6 carbon atoms), and/or (xix) a pyridylsulfonylamino group (the nitrogen atom of the amino moiety may be substituted with a straight or branched chain alkyl group having from 1 to 6 carbon atoms).

The substituents β represents a straight or branched chain alkyl group having from 1 to 6 carbon atoms, a straight or branched chain halogenoalkyl group having from 1 to 4 carbon atoms, a straight or branched chain alkoxy group having from 1 to 4 carbon atoms, a halogen atom or a straight or branched chain alkylenedioxy group having from 1 to 4 carbon atoms;

$Y^e$ represents an oxygen or sulfur atom or a group of formula >N—$R^{4e}$ (wherein $R^4$ represents a hydrogen atom, a straight or branched chain alkyl group having from 1 to 3 carbon atoms or a straight or branched chain alkanoyl group having from 2 to 5 carbon atoms); and $Z^e$ represents a 2,4-dioxothiazolidin-5-ylmethyl group, a 2,4-dioxooxazolidin-5-ylmethyl group or a 3,5-dioxooxadiazolidin-2-ylmethyl group,

(26) the compounds described in (1) in which $R^{1e}$ represents a hydrogen atom or a straight or branched chain alkyl group having from 1 to 4 carbon atoms;

$R^{2e}$ represents a straight or branched chain alkylene group having from 2 to 5 carbon atoms;

$R^{3e}$ represents a hydrogen atom;

$X^e$ represents an aryl group having from 6 to 10 carbon atoms which may have from 1 to 3 substituents α, or a 5- to 10-membered aromatic heterocyclic group (comprising one or two rings) having from 1 to 3 nitrogen atoms, oxygen atoms and/or sulfur atoms which may have from 1 to 3 substituents α.

The substituent α represents (i) a straight or branched chain alkyl group having from 1 to 6 carbon atoms, (ii) a straight or branched chain halogenoalkyl group having from 1 to 4 carbon atoms, (iii) a hydroxy group, (iv) a straight or branched chain alkanoyloxy group having from 1 to 4 carbon atoms, (v) a straight or branched chain alkoxy group having from 1 to 4 carbon atoms, (vi) a straight or branched chain alkylenedioxy group having from 1 to 4 carbon atoms, (vii) an aralkyloxy group having from 7 to 12 carbon atoms, (viii) a straight or branched chain alkylthio group having from 1 to 4 carbon atoms, (ix) a straight or branched chain alkylsulfonyl group having from 1 to 4 carbon atoms, (x) a fluorine, chlorine or bromine atom, (xi) an aralkyl group having from 7 to 12 carbon atoms, (xii) a phenyl group which may have a substituent β, (xiii) a phenoxy group which may have a substituent β, (xiv) a phenylthio group which may have a substituent β, (xv) a phenylsulfonyl group which may have a substituent β, (xvi) a phenylsulfonylamino group which may have a substituent β (the nitrogen atom of the amino moiety may be substituted with a straight or branched chain alkyl group having from 1 to 6 carbon atoms), (xvii) a furyl, thienyl, oxazolyl, isoxazolyl, thiazolyl, pyridyl, pyridyloxy, pyridylthio or pyridyisulfonyl group, (xviii) an imidazolyl group (the nitrogen atom may be substituted with a straight or branched chain alkyl group having from 1 to 6 carbon atoms), and/or (xix) a pyridylsulfonylamino group (the nitrogen atom of the amino moiety may be substituted with a straight or branched chain alkyl group having from 1 to 6 carbon atoms).

The substituents β represents a straight or branched chain alkyl group having from 1 to 6 carbon atoms, a straight or branched chain halogenoalkyl group having from 1 to 4 carbon atoms, a straight or branched chain alkoxy group having from 1 to 4 carbon atom, a halogen atom or a straight or branched chain alkylenedioxy group having from 1 to 4 carbon atoms;

$Y^e$ represents an oxygen atom; and $Z^e$ represents a 2,4-dioxothiazolidin-5-ylmethyl group or a 2,4-dioxooxazolidin-5-ylmethyl group,

(27) those described in (1) in which $R^{1e}$ represents a hydrogen atom or a straight or branched chain alkyl group having from 1 to 3 carbon atoms;

$R^{2e}$ represents a straight or branched chain alkylene group having from 2 to 3 carbon atoms;

$R^{3e}$ represents a hydrogen atom;

$X^e$ represents a phenyl, naphthyl, imidazolyl, oxazolyl, pyridyl, indolyl, quinolyl or isoquinolyl group, and these groups optionally having from 1 to 3 substituents α.

The substituent α represents (i) a straight or branched chain alkyl group having from 1 to 6 carbon atoms, (ii) a straight or branched chain halogenoalkyl group having from 1 to 4 carbon atoms, (iii) a hydroxy group, (iv) a straight or branched chain alkanoyloxy group having from 1 to 4 carbon atoms, (v) a straight or branched chain alkoxy group having from 1 to 4 carbon atoms, (vi) a methylenedioxy group, (vii) an aralkyloxy group having from 7 to 12 carbon atoms, (viii) a straight or branched chain alkylthio group having from 1 to 4 carbon atoms, (ix) a straight or branched chain alkylsulfonyl group having from 1 to 4 carbon atoms, (x) a fluorine, chlorine or bromine atom, (xi) an aralkyl group having from 7 to 12 carbon atoms, (xii) a phenyl group (the phenyl may be substituted with methyl, trifluoromethyl, methoxy, fluoro or methylenedioxy), (xiii) a phenoxy group (the phenyl group may be substituted with methyl, trifluoromethyl, methoxy, fluoro or methylenedioxy), (xiv) a phenylthio group (the phenyl group may be substituted with methyl, trifluoromethyl, methoxy, fluoro or methylenedioxy), (xv) a phenylsulfonyl group (the phenyl group may be substituted with methyl, trifluoromethyl, methoxy, fluoro or methylenedioxy), (xvi) a phenylsulfonylamino group (the phenyl group may be substituted with methyl, trifluoromethyl, methoxy, fluoro or methylenedioxy, and the nitrogen atom of the amino moiety may be substituted with a straight or branched chain alkyl group having from 1 to 6 carbon atoms), (xvii) a furyl, thienyl, oxazolyl, isoxazolyl, thiazolyl, pyridyl, pyridyloxy, pyridylthio or pyridylsulfonyl group, (xviii) an imidazolyl group (the nitrogen atom may be substituted with a straight or branched chain alkyl group having from 1 to 6 carbon atoms), and/or (xix) a pyridylsulfonylamino group (the nitrogen atom of the amino moiety may be substituted with a straight or branched chain alkyl group having from 1 to 6 carbon atoms), $Y^e$ represents an oxygen atom; and $Z^e$ represents a 2,4-dioxothiazolidin-5-ylmethyl group,

(28) those described in (1) in which $R^{1e}$ represents a hydrogen atom, a methyl group or ethyl group;

$R^{2e}$ represents an ethylene, trimethylene or methylethylene group;

$R^{3e}$ represents a hydrogen atom;

$X^e$ represents a phenyl, naphthyl, imidazolyl, oxazolyl, pyridyl, indolyl, quinolyl or isoquinolyl group and these groups optionally have from 1 to 3 substituent α.

The substituent α represents (i) a straight or branched chain alkyl group having from 1 to 6 carbon atoms, (ii) a straight or branched chain halogenoalkyl group having from 1 to 4 carbon atoms, (iii) a hydroxy group, (iv) a straight or branched chain alkanoyloxy group having from 1 to 4 carbon atoms, (v) a straight or branched chain alkoxy group having from 1 to 4 carbon atoms, (vi) a methylenedioxy, benzyloxy, phenethyloxy or naphthylmethoxy group, (vii) a straight or branched chain alkylthio group having from 1 to 4 carbon atoms, (viii) a straight or branched chain alkylsulfonyl group having from 1 to 4 carbon atoms, (ix) a fluorine, chlorine or bromine atom, (x) a benzyl group, (xi) a phenyl group (the phenyl may be substituted with methyl, trifluoromethyl, methoxy, fluoro or methylenedioxy), (xii) a phenoxy group (the phenyl group may be substituted with methyl, trifluoromethyl, methoxy, fluoro or methylenedioxy), (xiii) a phenylthio, phenylsulfonyl, phenylsulfonylamino, N-methylphenylsulfonylamino, furyl, thienyl, oxazolyl, isoxazolyl, thiazolyl, pyridyl, pyridyloxy, pyridylthio, pyridylsulfonyl, pyridylsulfonylamino or N-methylpyridylsulfonylamino group, and/or (xiv) an imidazolyl group (the nitrogen atom may be substituted with a straight or branched chain alkyl group having from 1 to 6 carbon atoms);

$Y^e$ represents an oxygen atom; and $Z^e$ represents an 2,4-dioxothiazolidin-5-ylmethyl group,

(29) those described in (1) in which $R^{1e}$ represents a hydrogen atom, a methyl group or an ethyl group;

$R^{2e}$ represents an ethylene, trimethylene or methylethylene group;

$R^{3e}$ represents a hydrogen atom, $X^e$ represents a phenyl, naphthyl, pyridyl, indolyl, quinolyl or isoquinolyl group and these groups optionally have from 1 to 3 substituent α.

The substituent α represents (i) a straight or branched chain alkyl group having from 1 to 3 carbon atoms, (ii) a trifluoromethyl, difluoromethyl, fluoromethyl, hydroxy, formyloxy or acetoxy group, (iii) a straight or branched chain alkoxy group having from 1 to 3 carbon atoms, (iv) a methylenedioxy, benzyloxy, methylthio, ethylthio, methylsulfonyl or ethylsulfonyl group, (v) a fluorine, chlorine or bromine atom, (vi) a benzyl, phenyl, 4-methylphenyl, 4-trifluoromethylphenyl, 4-methoxyphenyl, 4-fluorophenyl, 3,4-methylenedioxyphenyl, phenoxy, phenylthio, phenylsulfonyl, phenylsulfonylamino, N-methylphenylsulfonylamino, furyl, thienyl, oxazolyl, thiazolyl, imidazolyl, N-methylimidazolyl, pyridyl, pyridyloxy, pyridylthio, pyridylsulfonyl, pyridylsulfonylamino and/or N-methylpyridylsulfonylamino group;

$Y^e$ represents an oxygen atom; and $Z^e$ represents a 2,4-dioxothiazolidin-5-ylmethyl group,

(30) those described in (1) in which $R^{1e}$ represents a hydrogen atom, a methyl group or an ethyl group;

$R^{2e}$ represents an ethylene group;

$R^{3e}$ represents a hydrogen atom;

$X^e$ represents a phenyl, naphthyl, pyridyl, quinolyl or isoquinolyl group and these groups optionally have from 1 to 3 substituents α.

The substituent α represents a methyl, ethyl, isopropyl, trifluoromethyl, hydroxy, acetoxy, methoxy, ethoxy, isopropoxy, methylenedioxy, benzyloxy, methylthio, ethylthio, methylsulfonyl or ethylsulfonyl group, a chlorine atom, or a benzyl, phenyl, phenoxy, phenylthio, phenylsulfonyl, phenylsulfonylamino, N-methylphenylsulfonylamino, pyridyl, pyridyloxy, pyridylthio, pyridylsulfonyl, pyridylsulfonylamino and/or a N-methylpyridylsulfonylamino group;

$Y^e$ represents an oxygen atom; and $Z^e$ represents a 2,4-dioxothiazolidin-5-ylmethyl group,

(31) those described in (1) in which $R^{1e}$ represents a methyl or ethyl group;

$R^{2e}$ represents an ethylene group;

$R^{3e}$ represents a hydrogen atom;

$X^e$ represents a phenyl group which may have from 1 to 3 substituents α.

The substituent α represents a methyl, hydroxy or acetoxy group, a chlorine atom, or a benzyl, phenyl, phenoxy, phenylthio, phenylsulfonyl, phenylsulfonylamino, N-methylphenylsulfonylamino, pyridyl, pyridyloxy, pyridylthio and/or pyridylsulfonyl group;

$Y^e$ represents an oxygen atom; and $Z^e$ represents a 2,4-dioxothiazolidin-5-ylmethyl group,

(32) those described in (1) in which $R^{1e}$ represents a methyl or ethyl group;

$R^{2e}$ represents an ethylene group;

$R^{3e}$ represents a hydrogen atom;

$X^e$ represents a pyridyl group which may have from 1 to 3 substituents α.

The substituent α represents a methoxy, ethoxy, isopropoxy, benzyloxy, methylthio, ethylthio, methylsulfonyl, ethylsulfonyl, benzyl, phenyl, phenoxy, phenylthio, phenylsulfonyl, phenylsulfonylamino and/or N-methylphenylsulfonylamino group;

$Y^e$ represents an oxygen atom; and $Z^e$ represents a 2,4-dioxothiazolidin-5-ylmethyl group, and

(33) those described in (1) selected from i) 5-[4-[2-[[[1-(4-biphenylyl)ethylidene]amino]oxy]ethoxy]benzyl]thiazolidine-2,4-dione, ii) 5-[4-[2-[[[1-(4-phenylsulfonylphenyl)ethylidene]amino]oxy]ethoxy]benzyl]thiazolidine-2,4-dione, iii) 5-[4-[2-[[[1-[4-(2-pyridyl)phenyl]ethylidene]amino]oxy]ethoxy]benzyl]thiazolidine-2,4-dione (hereinafter referred to as "compound A"), iv) 5-[4-[2-[[[1-[4-(3-pyridyl)phenyl]ethylidene]amino]oxy]ethoxy]benzyl]thiazolidine-2,4-dione, v) 5-[4-[2-[[[1-[4-(4-pyridyl)phenyl]ethylidene]amino]oxy]ethoxy]benzyl]thiazolidine-2,4-dione, vi) 5-[4-[2-[[[1-(2-phenyl-5-pyridyl)ethylidene]amino]oxy]ethoxy]benzyl]thiazolidine-2,4-dione, vii) 5-[4-[2-[[[1-(2-methoxy-5-pyridyl)ethylidene]amino]oxy]ethoxy]benzyl]thiazolidine-2,4-dione, viii) 5-[4-[2-[[[1-(2-ethoxy-5-pyridyl)ethylidene]amino]oxy]ethoxy]benzyl]thiazolidine-2,4-dione, ix) 5-[4-[2-[[[1-(2-isopropoxy-5-pyridyl)ethylidene]amino]oxy]ethoxy]benzyl]thiazolidine-2,4-dione, and x) 5-[4-[2-[[[1-(2-benzyl-5-pyridyl)ethylidene]amino]oxy]ethoxy]benzyl]thiazolidine-2,4-dione.

(VI) In WO95/18125, there is disclosed (1) an isoxazolidinedione derivative of formula (VI):

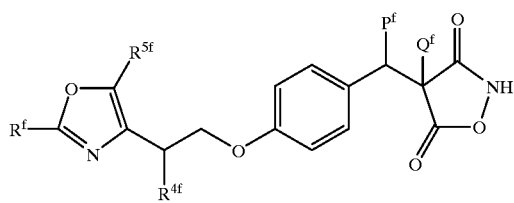

(VI)

[wherein $R^f$ represents an optionally substituted aromatic hydrocarbon group, an optionally substituted cycloaliphatic hydrocarbon group, an optionally substituted heterocyclic group, an optionally substituted condensed heterocylic group or a group of the following formula:

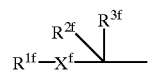

(wherein $R^{1f}$ represents an optionally substituted aromatic hydrocarbon group, an optionally substituted cycloaliphatic hydrocarbon group, an optionally substituted heterocyclic group or an optionally substituted condensed heterocyclic group, $R^{2f}$ and $R^{3f}$ may be the same or different and each represents a hydrogen atom or a lower alkyl group, and $X^f$ represents an oxygen atom, a sulfur atom or a secondary amino group), $R^{4f}$ represents a hydrogen atom or a lower alkyl group, $R^{5f}$ represents a lower alkyl group, and $P^f$ and $Q^f$ each represent a hydrogen atom or $P^f$ and $Q^f$ taken together represent a bond]

or a pharmacologically acceptable salt thereof.

In the compound of formula (VI), the details of the definition of $R^f$, $R^{1f}$, $R^{2f}$, $R^{3f}$, $R^{4f}$, $R^{5f}$, $P^f$ and $Q^f$, the kind of the pharmacologically acceptable salt, the process for preparation of the compound of the formula (VI), examples of the compounds, Examples, etc. are described in the above-mentioned publication.

Of which the compound of formula (VI), preferred compounds are shown below.

(2) those described in (1) in which $R^{4f}$ is a hydrogen atom and $R^{5f}$ is a lower alkyl group, (3) those described in (2) in which $R^f$ is an optionally substituted phenyl group, an optionally substituted 5- or 6-membered aromatic heterocyclic group containing one or two hetero atoms selected from sulfur, oxygen and nitrogen atoms or an optionally substituted condensed aromatic heterocyclic group in which the above-mentioned aromatic heterocyclic ring is condensed with a benzene ring, (4) those described in (3) in which $R^f$ is a phenyl group, a 5- or 6-membered aromatic heterocyclic group containing one or two hetero atoms selected from sulfur, oxygen and nitrogen atoms or a condensed aromatic heterocyclic group in which the above-mentioned aromatic heterocyclic ring is condensed with a benzene ring, (5) those described in (3) in which $R^f$ is a phenyl group or a condensed aromatic heterocyclic group in which a 5- or 6-membered heterocyclic ring containing a sulfur atom is condensed with a benzene ring, (6) those described in (2) in which $R^f$ is a phenyl, benzothienyl or 1-methyl-1-(2-pyridylthio)methyl group, (7) those described in (2) in which $R^f$ is a phenyl group, (8) those described in (2) in which $R^f$ is a group of the formula:

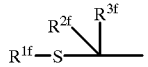

(9) those described in (8) in which $R^{1f}$ is an optionally substituted phenyl group or an optionally substituted 5- or 6-membered aromatic heterocyclic group containing one or two hetero atoms selected from sulfur, oxygen and nitrogen atoms,

(10) those described in (8) in which $R^{1f}$ is a 5- or 6-membered aromatic heterocyclic group containing one or two hetero atoms selected from sulfur, oxygen and nitrogen atoms,

(11) those described in (8) in which $R^{1f}$ is a 5- or 6-membered aromatic heterocyclic group containing a nitrogen atom,

(12) those described in (8) in which $R^{1f}$ is a pyridyl group,

(13) those described in (1) selected from i) 4-[4-[2-(2-phenyl-5-methyl-4-oxazolyl)ethoxy]benzyl]-3,5-isoxazolidinedione, ii) 4-[4-[2-(2-phenyl-5-methyl-4-oxazolyl)ethoxy]benzylidene]-3,5-isoxazolidinedione, iii) 4-[4-[2-(2-benzothienyl-5-methyl-4-oxazolyl)ethoxy]benzyl]-3,5-isoxazolidinedione, and iv) 4-[4-[2-[5-methyl-[2-(2-pyridylthio)ethyl-4-oxazolyl]
ethoxy]benzyl]-3,5-isoxazolidinedione.

(VII) In Japanese Patent Application (Kokai) No. Hei 7-330728 and European Patent No. 676398A, there is disclosed (1) a heterocyclic compound of formula (VII):

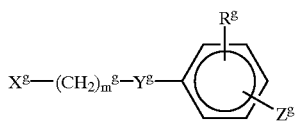

(VII)

[wherein $X^g$ represents an indole ring group, an indoline ring group, an azaindole ring group, an azaindoline ring group, an imidazopyridine ring group or an imidazopyrimidine ring group, and these ring groups may have from 1 to 3 substituent moieties (a) described later, $Y^g$ represents an oxygen or sulfur atom, $Z^g$ represents a 2,4-dioxothiazolidin-5-ylidenylmethyl, 2,4-dioxothiazolidin-5-ylmethyl, 2,4-dioxooxazolidin-5-ylmethyl, 3,5-dioxooxazolidin-2-ylmethyl or N-hydroxyureidomethyl group, $R^g$ represents a hydrogen atom, a straight or branched chain alkyl group having from 1 to 4 carbon atoms, a straight or branched chain alkoxy group having from 1 to 4 carbon atoms, a halogen atom, a hydroxy group, a nitro group, an amino group which may have a substituent (b) (the substituent (b) represents a straight or branched chain alkyl group having from 1 to 8 carbon atoms, a straight or branched chain aralkyl group having from 7 to 11 carbon atoms, an aryl group having from 6 to 10 carbon atoms, a straight or branched chain aliphatic acyl group having from 1 to 11 carbon atoms, an aroma-aliphatic acyl group having from 8 to 12 carbon atoms or an aromatic acyl group having from 7 to 11 carbon atoms) or a straight or branched chain aralkyl group having from 7 to 11 carbon atoms, $m^g$ is an integer of 1 to 5.

The substituent (a) represents a straight or branched chain alkyl group having from 1 to 4 carbon atoms, a straight or branched chain alkoxy group having from 1 to 4 carbon atoms, a benzyloxy group, a halogen atom, a hydroxy group, an acetoxy group, a phenylthio group, a straight or branched chain alkylthio group having from 1 to 4 carbon atoms, a trifluoromethyl group, a nitro group, an amino group which may have a substituent (b) (the substituent (b) represents a straight or branched chain alkyl group having from 1 to 8 carbon atoms, a straight or branched chain aralkyl group having from 7 to 11 carbon atoms, an aryl group having from 6 to 10 carbon atoms, a straight or branched chain aliphatic acyl group having from 1 to 11 carbon atoms, an aroma-aliphatic acyl group having from 8 to 12 carbon atoms or an aromatic acyl group having from 7 to 11 carbon atoms), an aryl group having from 6 to 10 carbon atoms which may have a substituent (c) (the substituent (c) represents a straight or branched chain alkyl group having from 1 to 4 carbon atoms, a straight or branched chain alkoxy group having from 1 to 4 carbon atoms, a halogen atom, a hydroxy group, a nitro group, a phenyl group, a trifluoromethyl group or an amino group which may have a substituent (b)) or a straight or branched chain aralkyl group having from 7 to 11 carbon atoms]

or a pharmacologically acceptable salt thereof.

In the compound of formula (VII), the details of the definition of $R^g$, $X^g$, $Y^g$, $Z^g$, the substituent (a), the substituent (b), the substituent (c) and mg, the kind of the pharmacologically acceptable salt, the process for preparation of the compound of the formula (VII), examples of the compounds, Examples, etc. are described in the above-mentioned publications.

Of which the compound of formula (VII), preferred compounds are shown below;

(2) those described in (1) in which $X^g$ represents an indole ring, indoline ring, azaindole ring, imidazopyridine ring or imidazopyrimidine ring group, and these rings may have from 1 to 3 substituents (a) described later.

The substituent (a) represents a straight or branched chain alkyl group having from 1 to 4 carbon atoms, a straight or branched chain alkoxy group having from 1 to 4 carbon atoms, a benzyloxy group, a halogen atom, a hydroxy group, an acetoxy group, a phenylthio group, a straight or branched chain alkylthio group having from 1 to 4 carbon atoms, a trifluoromethyl group, a nitro group, an amino group which may have a substituent (b) (the substituent (b) represents a straight or branched chain alkyl group having from 1 to 8 carbon atoms, a straight or branched chain aralkyl group having from 7 to 11 carbon atoms, an aryl group having from 6 to 10 carbon atoms, a straight or branched chain aliphatic acyl group having from 1 to 11 carbon atoms, an aroma-aliphatic acyl group having from 8 to 12 carbon atoms or an aromatic acyl group having from 7 to 11 carbon atoms), an aryl group having from 6 to 10 carbon atoms which may have at least one substituent (c) (the substituent (c) represents a straight or branched chain alkyl group having from 1 to 4 carbon atoms, a straight or branched chain alkoxy group having from 1 to 4 carbon atoms, a halogen atom, a hydroxy group, a nitro group, a phenyl group, a trifluoromethyl group or an amino group which may have a substituent (b)) or a straight or branched chain aralkyl group having from 7 to 11 carbon atoms which may have at least one substituent (c), (3) those described in (1) in which $X^g$ represents an indole ring, indoline ring, imidazopyridine ring or imidazopyrimidine ring group, and these rings may have from 1 to 3 substituents (a) described later.

The substituent (a) represents a straight or branched chain alkyl group having from 1 to 4 carbon atoms, a straight or branched chain alkoxy group having from 1 to 4 carbon atoms, a benzyloxy group, a halogen atom, a hydroxy group, an acetoxy group, a phenylthio group, a straight or branched chain alkylthio group having from 1 to 4 carbon atoms, a trifluoromethyl group, a nitro group, an amino group which may have a substituent (b) (the substituent (b) represents a straight or branched chain alkyl group having from 1 to 8 carbon atoms, a straight or branched chain aralkyl group having from 7 to 11 carbon atoms, an aryl group having from 6 to 10 carbon atoms, a straight or branched chain aliphatic acyl group having from 1 to 11 carbon atoms, an aroma-aliphatic acyl group having from 8 to 12 carbon atoms or an aromatic acyl group having from 7 to 11 carbon atoms), an aryl group having from 6 to 10 carbon atoms which may have at least one substituent (c) (the substituent (c) represents a straight or branched chain alkyl group having from 1 to 4 carbon atoms, a straight or branched chain alkoxy group having from 1 to 4 carbon atoms, a halogen atom, a hydroxy group, a nitro group, a phenyl group, a trifluoromethyl group or an amino group which may have a substituent (b)) or a straight or branched chain aralkyl group having from 7 to 11 carbon atoms which may have at least one substituent (c), (4) those described in (1) in which $X^g$ represents an indole ring, indoline ring or imidazopyridine ring group, and these rings may have from 1 to 3 substituents (a) described later.

The substituent (a) represents a straight or branched chain alkyl group having from 1 to 4 carbon atoms, a straight or branched chain alkoxy group having from 1 to 4 carbon atoms, a benzyloxy group, a halogen atom, a hydroxy group, an acetoxy group, a phenylthio group, a straight or branched chain alkylthio group having from 1 to 4 carbon atoms, a trifluoromethyl group, a nitro group, an amino group which may have a substituent (b) (the substituent (b) represents a straight or branched chain alkyl group having from 1 to 8 carbon atoms, a straight or branched chain aralkyl group having from 7 to 11 carbon atoms, an aryl group having from 6 to 10 carbon atoms, a straight or branched chain aliphatic acyl group having from 1 to 11 carbon atoms, an aromaaliphatic acyl group having from 8 to 12 carbon atoms or an aromatic acyl group having from 7 to 11 carbon atoms), an aryl group having from 6 to 10 carbon atoms which may have from 1 to 3 substituents (c) (the substituent (c) represents a straight or branched chain alkyl group having from 1 to 4 carbon atoms, a straight or branched chain alkoxy group having from 1 to 4 carbon atoms, a halogen atom, a hydroxy group, a nitro group, a phenyl group, a trifluoromethyl group or an amino group which may have a substituent (b)) or a straight or branched chain aralkyl group having from 7 to 11 carbon atoms which may have from 1 to 3 substituents (c), (5) those described in (1) in which $X^g$ represents an indoline ring or imidazopyridine ring group, and these rings may have from 1 to 3 substituents (a) described later.

The substituent (a) represents a straight or branched chain alkyl group having from 1 to 4 carbon atoms, a straight or branched chain alkoxy group having from 1 to 4 carbon atoms, a benzyloxy group, a halogen atom, a phenylthio group, a straight or branched chain alkylthio group having from 1 to 4 carbon atoms, a trifluoromethyl group or a phenyl group, (6) those described in (1) in which $X^g$ represents an imidazopyridine ring group, and the ring may have from 1 to 3 substituents (a) described later.

The substituent (a) represents a methyl, ethyl, isopropyl, methoxy, ethoxy, propoxy, isopropoxy or benzyloxy group, a fluorine or chlorine atom, or a phenylthio, methylthio, ethylthio or phenyl group, (7) those described in (1) in which $R^g$ represents a hydrogen atom, a straight or branched chain alkyl group having from 1 to 4 carbon atoms, a straight or branched chain alkoxy group having from 1 to 4 carbon atoms or a halogen atom, (8) those described in (1) in which $R^g$ represents a hydrogen atom, a methoxy group, an ethoxy group, a fluorine atom or a chlorine atom, (9) those described in (1) in which $R^g$ represents a hydrogen atom or a methoxy group,

(10) those described in (1) in which $R^g$ represents a hydrogen atom,

(11) those described in (1) in which $Y^g$ represents an oxygen atom,

(12) those described in (1) in which $Z^g$ represents a 2,4-dioxothiazolidin-5-ylidenylmethyl, 2,4-dioxothiazolidin-5-ylmethyl or 2,4-dioxooxazolidin-5-ylmethyl group,

(13) those described in (1) in which $Z^g$ represents a 2,4-dioxothiazolidin-5-ylidenylmethyl or 2,4-dioxothiazolidin-5-ylmethyl group,

(14) those described in (1) in which $Z^g$ represents a 2,4-dioxothiazolidin-5-ylmethyl,

(15) those described in (1) in which $X^g$ represents an indole ring, indoline ring, azaindole ring, imidazopyridine ring or imidazopyrimidine ring group, and these rings may have from 1 to 3 substituents (a) described later, $Y^g$ represents an oxygen or sulfur atom, $Z^g$ represents a 2,4-dioxothiazolidin-5-ylidenylmethyl, 2,4-dioxothiazolidin-5-ylmethyl, 2,4-dioxooxazolidin-5-ylmethyl, 3,5-dioxooxadiazolidin-2-ylmethyl or N-hydroxyureidomethyl group, $R^g$ represents a hydrogen atom, a straight or branched chain alkyl group having from 1 to 4 carbon atoms, a straight or branched chain alkoxy group having from 1 to 4 carbon atoms or a halogen atom, $m^g$ represents an integer of 1 to 5.

The substituent (a) represents a straight or branched chain alkyl group having from 1 to 4 carbon atoms, a straight or branched chain alkoxy group having from 1 to 4 carbon atoms, a benzyloxy group, a halogen atom, a hydroxy group, an acetoxy group, a phenylthio group, a straight or branched chain alkylthio group having from 1 to 4 carbon atoms, a trifluoromethyl group, a nitro group, an amino group which may have a substituent (b) (the substituent (b) represents a straight or branched chain alkyl group having from 1 to 8 carbon atoms, a straight or branched chain aralkyl group having from 7 to 11 carbon atoms, an aryl group having from 6 to 10 carbon atoms, a straight or branched chain aliphatic acyl group having from 1 to 11 carbon atoms, an aromaaliphatic acyl group having from 8 to 12 carbon atoms or an aromatic acyl group having from 7 to 11 carbon atoms), an aryl group having from 6 to 10 carbon atoms which may have at least one substituent (c) (the substituent (c) represents a straight or branched chain alkyl group having from 1 to 4 carbon atoms, a straight or branched chain alkoxy group having from 1 to 4 carbon atoms, a halogen atom, a hydroxy group, a nitro group, a phenyl group, a trifluoromethyl group or an amino group which may have a substituent (b)), or a straight or branched chain aralkyl group having from 7 to 11 carbon atoms which may have at least one substituent (c),

(16) those described in (1) in which $X^6$ represents an indole ring, indoline ring, imidazopyridine ring or imidazopyrimidine ring group, and these rings may have from 1 to 3 substituents (a) described later, $Y^g$ represents an oxygen atom, $Z^g$ represents a 2,4-dioxothiazolidin-5-ylidenylmethyl, 2,4-dioxothiazolidin-5-ylmethyl or 2,4-dioxooxazolidin-5-ylmethyl group, $R^g$ represents a hydrogen atom, a straight or branched chain alkyl group having from 1 to 4 carbon atoms, a straight or branched chain alkoxy group having from 1 to 4 carbon atoms or a halogen atom, $m^g$ represents an integer of 1 to 5.

The substituent (a) represents a straight or branched chain alkyl group having from 1 to 4 carbon atoms, a straight or branched chain alkoxy group having from 1 to 4 carbon atoms, a benzyloxy group, a halogen atom, a hydroxy group, an acetoxy group, a phenylthio group, a straight or branched chain alkylthio group having from 1 to 4 carbon atoms, a trifluoromethyl group, a nitro group, an amino group which may have a substituent (b) (the substituent (b) represents a straight or branched chain alkyl group having from 1 to 8 carbon atoms, a straight or branched chain aralkyl group having from 7 to 11 carbon atoms, an aryl group having from 6 to 10 carbon atoms, a straight or branched chain aliphatic acyl group having from 1 to 11 carbon atoms, an aroma-aliphatic acyl group having from 8 to 12 carbon atoms or an aromatic acyl group having from 7 to 11 carbon atoms), an aryl group having from 6 to 10 carbon atoms which may have at least one substituent (c) (the substituent (c) represents a straight or branched chain alkyl group having from 1 to 4 carbon atoms, a straight or branched chain alkoxy group having from 1 to 4 carbon atoms, a halogen atom, a hydroxy group, a nitro group, a phenyl group, a trifluoromethyl group or an amino group which may have a substituent (b)), or a straight or branched chain aralkyl group having from 7 to 11 carbon atoms which may have at least one substituent (c),

(17) the compound described in (1) in which $X^g$ represents an indole ring, an indoline ring or imidazopyridine ring group, and these rings may have from 1 to 3 substituents (a) described later, $Y^g$ represents an oxygen atom, $Z^g$ represents a 2,4-dioxothiazolidin-5-ylidenylmethyl or 2,4-dioxothiazolidin-5-ylmethyl group, $R^g$ represents a hydrogen atom, a methoxy group, an ethoxy group, a fluorine atom or a chlorine atom, $m^g$ represents an integer of 1 to 5.

The substituent (a) represents a straight or branched chain alkyl group having from 1 to 4 carbon atoms, a straight or branched chain alkoxy group having from 1 to 4 carbon atoms, a benzyloxy group, a halogen atom, a hydroxy group, an acetoxy group, a phenylthio group, a straight or branched chain alkylthio group having from 1 to 4 carbon atoms, a trifluoromethyl group, a nitro group, an amino group which may have a substituent (b) (the substituent (b) represents a straight or branched chain alkyl group having from 1 to 8 carbon atoms, a straight or branched chain aralkyl group having from 7 to 11 carbon atoms, an aryl group having from 6 to 10 carbon atoms, a straight or branched chain aliphatic acyl group having from 1 to 11 carbon atoms, an aroma-aliphatic acyl group having from 8 to 12 carbon atoms or an aromatic acyl group having from 7 to 11 carbon atoms), an aryl group having from 6 to 10 carbon atoms which may have at least one substituent (c) (the substituent (c) represents a straight or branched chain alkyl group having from 1 to 4 carbon atoms, a straight or branched chain alkoxy group having from 1 to 4 carbon atoms, a halogen atom, a hydroxy group, a nitro group, a phenyl group, a trifluoromethyl group or an amino group which may have a substituent (b)) or a straight or branched chain aralkyl group having from 7 to 11 carbon atoms which may have from 1 to 3 substituents (c),

(18) those described in (1) in which $X^g$ represents an indoline ring or imidazopyridine ring group, and these rings may have from 1 to 3 substituents (a) described later, $Y^g$ represents an oxygen atom, $Z^g$ represents a 2,4-dioxothiazolidin-5-ylmethyl group, $R^g$ represents a hydrogen atom or a methoxy group, $m^g$ represents an integer of 1 to 5.

The substituent (a) represents a straight or branched chain alkyl group having from 1 to 4 carbon atoms, a straight or branched chain alkoxy group having from 1 to 4 carbon atoms, a benzyloxy group, a halogen atom, a phenylthio group, a straight or branched chain alkylthio group having from 1 to 4 carbon atoms, a trifluoromethyl group or a phenyl group,

(19) those described in (1) in which $X^g$ represent s an imidazopyridine ring group, and the ring may have from 1 to 3 substituents (a) described later, $Y^g$ represents an oxygen atom, $Z^g$ represents a 2,4-dioxothiazolidin-5-ylmethyl group, $R^g$ represents a hydrogen atom, $m^g$ represents an integer of 1 to 5.

The substituent (a) represents a methyl, ethyl, isopropyl, methoxy, ethoxy, propoxy, isopropoxy or benzyloxy group, a fluorine or chlorine atom, or a phenylthio, methylthio, ethylthio or phenyl group,

(20) those described in (1) selected from
  i) 5-{4-(3-methylimidazo[4,5-b]pyridin-2-ylmethoxy)benzyl}thiazolidine-2,4-dione,
  ii) 5-[4-(5-chloro-3-methylimidazo[4,5-b]pyridin-2-ylmethoxy)benzyl]thiazolidine-2,4-dione,
  iii) 5-[4-(5-methoxy-3-methylimidazo[4,5-b]pyridin-2-ylmethoxy)benzyl]thiazolidine-2,4-dione,
  iv) 5-[4-(5-hydroxy-3-methylimidazo[4,5-b]pyridin-2-ylmethoxy)benzyl]thiazolidine-2,4-dione,
  v) 5-[4-(5-ethoxy-3-methylimidazo[4,5-b]pyridin-2-ylmethoxy)benzyl]thiazolidine-2,4-dione,
  vi) 5-[4-(5-isopropoxy-3-methylimidazo[4,5-b]pyridin-2-ylmethoxy)benzyl]thiazolidine-2,4-dione, and
  vii) 5-[4-(1-methylindolin-2-ylmethoxy)benzyl]thiazolidine-2,4-dione.

(VIII) In European Patent No. 745600A, there is described (1) a condensed heterocyclic compound of the formula (VIII):

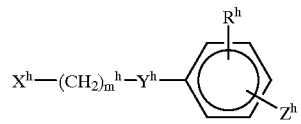

(VIII)

[wherein $X^h$ represents a benzimidazole ring group, and the group may have from 1 to 5 substituents (a) described later, $Y^h$ represents an oxygen or sulfur atom, $Z^h$ represents a 2,4-dioxothiazolidin-5-ylidenylmethyl, 2,4-dioxothiazolidin-5-ylmethyl, 2,4-dioxooxazolidin-5-ylmethyl, 3,5-dioxooxadiazolidin-2-ylmethyl or N-hydroxyureidomethyl group, $R^h$ represents a hydrogen atom, a straight or branched chain alkyl group having from 1 to 4 carbon atoms, a straight or branched chain alkoxy group having from 1 to 4 carbon atoms, a halogen atom, a hydroxy group, a nitro group, an amino group which may have a substituent (b) (the substituent (b) represents a straight or branched chain alkyl group having from 1 to 8 carbon atoms, a straight or branched chain aralkyl group having from 7 to 11 carbon atoms, an aryl group having from 6 to 10 carbon atoms, a straight or branched chain aliphatic acyl group having from 1 to 11 carbon atoms, an aroma-aliphatic acyl group having from 8 to 12 carbon atoms or an aromatic acyl group having from 7 to 11 carbon atoms) or a straight or branched chain aralkyl group having from 7 to 11 carbon atoms, $m^h$ is an integer of 1 to 5.

The substituent (a) represents a straight or branched chain alkyl group having from 1 to 4 carbon atoms, a straight or branched chain alkoxy group having from 1 to 4 carbon atoms, a benzyloxy group, a halogen atom, a hydroxy group, an acetoxy group, a phenylthio group, a straight or branched chain alkylthio group having from 1 to 4 carbon atoms, a trifluoromethyl group, a nitro group, an amino group which may have a substituent (b) (the substituent (b) represents a straight or branched chain alkyl group having from 1 to 8 carbon atoms, a straight or branched chain aralkyl group having from 7 to 11 carbon atoms, an aryl group having from 6 to 10 carbon atoms, a straight or branched chain aliphatic acyl group having from 1 to 11 carbon atoms, an aromaaliphatic acyl group having from 8 to 12 carbon atoms or an aromatic acyl group having from 7 to 11 carbon atoms), an aryl group having from 6 to 10 carbon atoms which may have a substituent (c) (the substituent (c) represents a straight or branched chain alkyl group having from 1 to 4 carbon atoms, a straight or branched chain alkoxy group having from 1 to 4 carbon atoms, a halogen atom, a hydroxy group, a nitro group, a phenyl group, a trifluoromethyl group or an amino group which may have a substituent (b)), or a straight or branched chain aralkyl group having from 7 to 11 carbon atoms which may have a substituent (c)], or a pharmacologically acceptable salt thereof.

In the compound of formula (VIII), the details of the definition of $R^h$, $X^h$, $Y^h$, $Z^h$, the substituent (a), the substituent (b), the substituent (c) and $m^h$, the kind of the pharmacologically acceptable salt, the process for preparation of the compound of the formula (VIII), examples of the compounds, Examples, etc. are described in the above-mentioned publication.

Of which the compound of formula (VIII), preferred compounds are shown below:

(2) those described in (1) in which $R^h$ represents a hydrogen atom, a straight or branched chain alkyl group having from 1 to 4 carbon atoms, a straight or branched chain alkoxy group having from 1 to 4 carbon atoms or a halogen atom, (3) those described in (1) in which $Y^h$ represents an oxygen atom, (4) those described in (1) in which $Z^h$ represents a 2,4-dioxothiazolidin-5-ylmethyl, 2,4-dioxothiazolidin-5-ylidenylmethyl or 2,4-dioxooxazolidin-5-ylmethyl group, (5) those described in (1) in which $R^h$ represents a hydrogen atom, a straight or branched chain alkyl group having from 1 to 4 carbon atoms, a straight or branched chain alkoxy group having from 1 to 4 carbon atoms or a halogen atom, $Y^h$ represents an oxygen atom, and $Z^h$ represents a 2,4-dioxothiazolidin-5-ylmethyl, 2,4-dioxothiazolidin-5-ylidenylmethyl or 2,4-dioxooxazolidin-5-ylmethyl group, (6) those described in (1) in which $Z^h$ represents a 2,4-dioxothiazolidin-5-ylmethyl or 2,4-dioxothiazolidin-5-ylidenylmethyl group, (7) those described in (1) in which $R^h$ represents a hydrogen atom, a methyl group, a methoxy group, an ethoxy group, a fluorine or chlorine atom, (8) those described in (1) in which $m^h$ is an integer of 1 to 3, (9) those described in (1) in which $Y^h$ is an oxygen atom, $Z^h$ represents a 2,4-dioxothiazolidin-5-ylmethyl or 2,4-dioxothiazolidin-5-ylidenylmethyl group, $R^h$ represents a hydrogen atom, a methyl group, a methoxy group, an ethoxy group, a fluorine or chlorine atom, and $m^h$ is an integer of 1 to 3,

(10) those described in (1) in which $X^h$ represents a benzimidazole ring group which may have from 1 to 5 substituents (a) described below, the substituent (a) represents a straight or branched chain alkyl group having from 1 to 4 carbon atoms, a straight or branched chain alkoxy group having from 1 to 4 carbon atoms, a benzyloxy group, a halogen atom, a phenylthio group, a straight or branched chain alkylthio group having from 1 to 4 carbon atoms, a trifluoromethyl group, a hydroxy group, an acetoxy group, a benzyl group or a phenyl group,

(11) those described in (1) in which $Z^h$ represents a 2,4-dioxooxazolidin-5-ylmethyl group,

(12) those described in (1) in which $R^h$ represents a hydrogen atom, a methyl group or a methoxy group,

(13) those described in (1) in which $X^h$ represents a benzimidazole ring group which may have from 1 to 5 substituents (a), the substituent (a) represents a straight or branched chain alkyl group having, from 1 to 4 carbon atoms, a straight or branched chain alkoxy group having from 1 to 4 carbon atoms, a benzyloxy group, a halogen atom, a phenylthio group, a straight or branched chain alkylthio group having from 1 to 4 carbon atoms, a trifluoromethyl group, a hydroxy group, an acetoxy group, a benzyl group or a phenyl group, $Y^h$ represents an oxygen atom, $Z^h$ represents a 2,4-dioxooxazolidin-5-ylmethyl group, $R^h$ represents a hydrogen atom, or a methyl or methoxy group, and $m^h$ is an integer of 1 to 3,

(14) those described in (1) in which $X^h$ represents a benzimidazole ring group which may have from 1 to 5 substituents (a), the substituent (a) represents a methyl, ethyl, isopropyl, methoxy, ethoxy, propoxy, isopropoxy or benzyloxy group, a fluorine or chlorine atom, or a phenylthio, methylthio, ethylthio, hydroxy, acetoxy, benzyl or phenyl group,

(15) those described in (1) in which $R^h$ represents a hydrogen atom,

(16) those described in (1) in which $m^h$ is 1 or 2,

(17) those described in (1) in which $X^h$ represents a benzimidazole ring group which may have from 1 to 5 substituents (a), the substituent (a) represents a methyl, ethyl, isopropyl, methoxy, ethoxy, propoxy, isopropoxy or benzyloxy group, a fluorine or chlorine atom, or a phenylthio, methylthio, ethylthio, hydroxy, acetoxy, benzyl or phenyl group, $Y^h$ represents an oxygen atom, $Z^h$ represents a 2,4-dioxothiazolidin-5-ylmethyl group, $R^h$ represents a hydrogen atom, and $m^h$ is 1 or 2,

(18) those described in (1) in which $X^h$ represents a benzimidazole ring group which may have from 1 to 5 substituents (a), the substituent (a) represents a methyl, methoxy, hydroxy, acetoxy or benzyl group,

(19) those described in (1) in which $m^h$ is 1,

(20) those described in (1) in which $X^h$ represents a benzimidazole ring group which may have from 1 to 5 substituents (a), the substituent (a) represents a methyl, methoxy, hydroxy, acetoxy or benzyl group, $Y^h$ represents an oxygen atom, $Z^h$ represents a 2,4-dioxothiazolidin-5-ylmethyl group, $R^h$ represents a hydrogen atom, and

(21) those described in (1) selected from
i) 5-[4-(1-methylbenzimidazol-2-ylmethoxy)benzyl]thiazolidine-2,4-dione,
ii) 5-[4-(6-methoxy-1-methylbenzimidazol-2-ylmethoxy)benzyl]thiazolidine-2,4-dione (hereinafter referred to as "compound B"),
iii) 5-[4-(5-methoxy-1-methylbenzimidazol-2-ylmethoxy)benzyl]thiazolidine-2,4-dione,
iv) 5-[4-(1-benzylbenzimidazol-5-ylmethoxy)benzyl]thiazolidine-2,4-dione,
v) 5-[4-(5-hydroxy-1,4,6,7-tetramethylbenzimidazol-2-ylmethoxy)benzyl]thiazolidine-2,4-dione, and
vi) 5-[4-(5-acetoxy-1,4,6,7-tetramethylbenzimidazol-2-ylmethoxy)benzyl]thiazolidine-2,4-dione.

(IX) In Japanese Patent Application (Kokai) No. Hei 1-272574 and European Patent No. 332332A, there is disclosed
(1) a compound of formula (IX):

(IX)

[wherein
the broken line represents a bond or a non-bond,
$V^i$ is —CH═CH—, —N═CH—, —CH═N— or S,
$W^i$ is $CH_2$, CHOH, CO, C═$NOR^i$ or CH═CH,
$X^i$ is S, O, $NR^{1i}$, —CH═N— or —N═CH—,
$Y^i$ is CH or N,
$Z^i$ is hydrogen, ($C_1$–$C_7$)alkyl, ($C_3$–$C_7$)cycloalkyl, phenyl, naphthyl, pyridyl, furyl, thienyl or phenyl substituted with one or two substituents chosen from ($C_1$–$C_3$)alkyl, trifluoromethyl, and ($C_1$–$C_3$)alkoxy groups, and fluoro, chloro or bromo atoms which substituents may be the same or different,
$Z^{h\ 1i}$ is hydrogen or ($C_1$–$C_3$)alkyl,
$R^i$ and $R^{1i}$ each independently represent hydrogen or methyl, and
$n^i$ is 1, 2 or 3]
or a pharmacologically acceptable salt thereof.

In the compound of the formula (IX), the details of the definition of $V^i$, $W^i$, $X^i$, $Y^i$, $Z^i$, $Z^{1i}$, $R^1$, $R^{1i}$ and $n^i$, the kind of the pharmacologically acceptable salt, the process for preparation of the compound of formula (IX), examples of the compounds, Examples, etc. are described in the above-mentioned publications.

Of which the compound of formula (IX), preferred compounds are shown below:
(2) those described in (1) in which the broken line represents a non-bond and $W^i$ is CO or CHOH,
(3) those described in (2) in which $V^i$ is —CH═CH—, —CH═N— or S, and $n^i$ is 2,
(4) those described in (3) in which $X^i$ is O and $Y^i$ is N to form an oxazol-4-yl group, $Z^i$ is (2-thienyl), (2-furyl), phenyl, substituted phenyl or naphthyl, and $Z^{1i}$ is 5-methyl,
(5) those described in (4) in which $V^i$ is —CH═N— or S, and $Z^i$ is 2-phenyl,
(6) those described in (1) in which $V^i$ is —CH═CH—, $W^i$ is CO, and $Z^i$ is 2-(2-furyl), 2-phenyl, 2-(4-methylphenyl) or 2-(2-naphthyl),
(7) those described in (3) in which $X^i$ is O or S, and $Y^i$ is N to form an oxazol-5-yl group, thiazol-4-yl or thiazol-5-yl group,
(8) those described in (3) in which $X^i$ is —CH═N—, and $Y^i$ is CH to form a pyrid-2-yl group, or $X^i$ is O, and $Y^i$ is CH to form a fur-2-yl group,
(9) those described in (1) which is 5-{4-[3-(5-methyl-2-phenyloxazol-4-yl)propionyl]benzyl}thiazolidine-2,4-dione.

(X) In Japanese Patent Application (Kokai) No. Hei 6-247945 and European Patent No. 604983A, there is disclosed
(1) a naphthalene derivative of the formula (X):

(X)

wherein $A^j$ represents

—$X^j$— represents —O— or —S—,
═$Y^j$— represents ═NH— or ═$CR^{5j}$—,
$R^{1j}$, $R^{2j}$, $R^{3j}$, $R^{4j}$ and $R^{5j}$ each independently represent a hydrogen atom, a halogen atom, an alkyl, aryl, alkoxy, alkoxyalkoxy, aryloxy, alkanoyloxy, arylcarbonyloxy, carboxyl, alkoxycarbonyl, aryloxycarbonyl, carbamoyl, alkylaminocarbonyl, arylaminocarbonyl, amino, alkylamino, alkanoylamino, arylcarbonylamino, ethylenedioxymethyl, formyl, cyano, nitro or trihalomethyl group,
$R^{6j}$ represents a hydrogen atom, an optionally substituted alkyl group or an optionally substituted aryl group,
$n^j$ is an integer of 0 to 3, and
the broken line represents a bond which may be a double bond]
or a pharmacologically acceptable salt thereof.

In the compound of formula (X), the details of the definition of $A^j$, $X^j$, $Y^j$, $R^{1j}$, $R^{2j}$, $R^{3j}$, $R^{4j}$, $R^{5j}$, $R^{6j}$ and $n^j$, the kind of the pharmacologically acceptable salt, the process for preparation of the compound of formula (X), examples of the compounds, Examples, etc. are described in the above-mentioned publications.

Of which the compound of formula (X), preferred compounds are shown below:
(2) those described in (1) in which $R^{1j}$, $R^{2j}$, $R^{3j}$, $R^{4j}$ and $R^{5j}$ each independently represent a hydrogen atom, a halogen atom, or a $C_1$–$C_8$ alkyl, $C_6$–$C_{12}$ aryl, $C_1$–$C_8$ alkoxy, $C_2$–$C_6$ alkoxyalkoxy, $C_6$–$C_{12}$ aryloxy, $C_2$–$C_9$ alkanoyloxy, $C_7$–$C_{13}$ arylcarbonyloxy, carboxyl, $C_{2-C9}$ alkoxycarbonyl, $C_7$–$C_{13}$ aryloxycarbonyl, carbamoyl, $C_{2-C9}$ alkylaminocarbonyl, $C_7$–$C_{13}$ arylaminocarbonyl, amino, $C_1$–$C_8$ alkylamino, $C_{2-C9}$ alkanoylamino, $C_7$–$C_{13}$ arylcarbonylamino, ethylenedioxymethyl, formyl, cyano, nitro or trihalomethyl group, and $R^{6j}$ represents a hydrogen atom; a $C_1$–$C_8$ alkyl group which may have one or more substituents selected from a phenyl group, a halogen atom, a nitro group and a cyano group; or a $C_6$–$C_{12}$ aryl group which may have one or more substituents selected from a $C_1$–$C_8$ alkyl group, a halogen atom, a nitro group and a cyano group, (3) those described in (1) in which $R^{1j}$, $R^{2j}$, $R^{3j}$, $R^{4j}$ and $R^{5j}$ each independently represent a hydrogen atom, a halogen atom, or a $C_1$–$C_8$ alkyl, $C_1$–$C_8$ alkoxy, $C_2$–$C_6$ alkoxyalkoxy, $C_2$–$C_9$ alkanoyloxy, $C_7$–$C_{13}$ arylcarbonyloxy, carboxyl, $C_2$–$C_9$ alkoxycarbonyl, carbamoyl, $C_2$–$C_9$ alkylaminocarbonyl, $C_7$–$C_{13}$ arylaminocarbonyl, amino, $C_1$–$C_8$ alkylamino, $C_2$–$C_9$ alkanoylamino, $C_7$–$C_{13}$ arylcarbonylamino, ethylenedioxymethyl, formyl, cyano, nitro or trihalomethyl group, and $R^{6j}$ represents a hydrogen atom; a $C_1$–$C_8$ alkyl group; or a $C_6$–$C_{12}$ aryl group which may be substituted with a halogen atom, (4) those described in (1) in which —$X^j$— represents —O—, $Y^j$ represents =$CR^{5j}$—, $R^{1j}$, $R^{2j}$, $R^{3j}$, $R^{4j}$ and $R^{5j}$ each independently represent a hydrogen atom, a halogen atom, or a $C_1$–$C_5$ alkyl, $C_1$–$C_5$ alkoxy, $C_2$–$C_6$ alkoxyalkoxy, $C_2$–$C_6$ alkanoyloxy, carboxyl, $C_2$–$C_6$ alkoxycarbonyl, $C_7$–$C_{13}$ arylaminocarbonyl, amino, $C_2$–$C_6$ alkanoylamino, ethylenedioxymethyl, formyl, cyano, nitro or trihalomethyl group, and $R^{6j}$ represents a hydrogen atom; a $C_1$–$C_5$ alkyl group; or a $C_6$–$C_{12}$ aryl group which may be substituted with a halogen atom, (5) those described in (1) in which

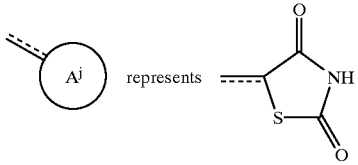

—$X^j$— represents —O—, $Y^j$ represents =$CR^{5j}$—, $R^{1j}$, $R^{2j}$, $R^{3j}$, and $R^{4j}$ each independently represent a hydrogen atom or a halogen atom, $R^{5j}$ represent a hydrogen atom, $R^{6j}$ represents a hydrogen atom, $n^j$ is 1, and the broken line represents a bond which is a single bond, or (6) those described in (1) which is 5-[6-(2-fluorobenzyloxy)-2-naphthylmethyl]thiazolidine-2,4-dione.

It should be noted that, in the compounds of the formulae (I) to (X) or pharmacologically acceptable salts thereof, in the case where various isomers, for example, the stereoisomers relating from the asymmetric carbon atoms exist (for example, the carbon atoms at the 2-position of the chromane ring and the 5-position of the thiazolidine ring of the compound of the formula (I) are the asymmetric carbon atoms), the stereoisomers resulting from these asymmetric carbon atoms and mixtures containing an equal or non-equal amount of these isomers are all represented by the single formula in the formulae (I) to (X). Therefore, the active ingredients of the present invention also include all of these isomers and the mixture of these isomers.

Further, in the compounds of the formulae (I) to (X) or pharmacologically acceptable salts thereof, for example, in the 2,4-dioxothiazolidin-5-yl ring, existence of various tautomers can be contemplated. In the formulae (I) to (X), all the tautomers and mixtures containing an equal or non-equal amount of these isomers are represented by the single formula. Therefore, the present invention includes all of these isomers and the mixtures of these isomers.

Further, in the present invention, in the case where the compounds of the formulae (I) to (X) or pharmacologically acceptable salts thereof form solvates (for example, hydrates), such solvates are also included in the present invention. For example, when the compounds of the formulae (I) to (X) or the pharmacologically acceptable salts thereof are left to stand in the atmosphere or recrystalized, they absorb moisture to carry adsorbed water or to form hydrates. Such solvates are also included in the present invention.

Further, the present invention includes all the compounds which are converted to those of the formulae (I) to (X) or pharmacologically acceptable salts thereof by being metabolized in the living body, that is, prodrugs.

The compounds of the formulae (I) to (X) of the present invention include preferably i) 5-[4-(6-hydroxy-2,5,7,8-tetramethylchroman-2-ylmethoxy)benzyl]thiazolidine-2,4-dione (troglitazone), ii) 5-[4-(6-hydroxy-2-methyl-7-t-butylchroman-2-ylmethoxy)benzyl]thiazolidine-2,4-dione, iii) 5-[4-(6-hydroxy-2-ethyl-5,7,8-trimethylchroman-2-ylmethoxy)benzyl]thiazolidine-2,4-dione, iv) 5-[4-(6-hydroxy-2-isobutyl-5,7,8-trimethylchroman-2-ylmethoxy)benzyl]thiazolidine-2,4-dione, v) 5-[4-(6-acetoxy-2,5,7,8-tetramethylchroman-2-ylmethoxy)benzyl]thiazolidine-2,4-dione, vi) 5-[4-(6-ethoxycarbonyloxy-2,5,7,8-tetramethylchroman-2-ylmethoxy)benzyl]thiazolidine-2,4-dione, vii) 5-{4-[2-(3-ethyl-2-pyridyl)ethoxy]benzyl}-2,4-thiazolidinedione, viii) 5-{4-[2-(4-ethyl-2-pyridyl)ethoxy]benzyl}-2,4-thiazolidinedione, ix) 5-{4-[2-(5-ethyl-2-pyridyl)ethoxy]benzyl}-2,4-thiazolidinedione (pioglitazone), x) 5-{4-[2-(6-ethyl-2-pyridyl)ethoxy]benzyl}-2,4-thiazolidinedione, xi) 5-[(2-benzyl-2,3-dihydrobenzofuran-5-yl)methyl]thiazolidine-2,4-dione, xii) 5-[(2-benzyl-3,4-dihydro-2H-benzopyran-6-yl)methyl]thiazolidine-2,4-dione (englitazone), xiii) 5-{4-[2-(N-methyl-N-(2-benzothiazolyl)amino)ethoxy]benzyl}thiazolidine-2,4-dione, xiv) 5-{4-[2-(N-methyl-N-(2-pyrimidinyl)amino)ethoxy]benzyl}thiazolidine-2,4-dione, xv) 5-{4-[2-(N-methyl-N-(2-[4,5-dim ethylthiazolyl)]amino)ethoxy]benzyl}thiazolidine-2,4-dione, xvi) 5-{4-[2-(N-methyl-N-(2-thiazolyl)amino)ethoxy]benzyl}thiazolidine-2,4-dione, xvii) 5-{4-[2-(N-methyl-N-(2-[4-phenylthiazolyl])amino)ethoxy]benzyl}thiazolidine-2,4-dione, xviii) 5-{4-[2-(N-methyl-N-(2-[4-phenyl-5-methylthiazolyl])amino)ethoxy]benzyl}thiazolidine-2,4-dione, xix) 5-{4-[2-(N-methyl-N-(2-[4-methyl-5-phenylthiazolyl])amino)ethoxy]benzyl}thiazolidine-2,4-dione, xx) 5-{4-[2-(N-methyl-N-(2-[5-phenyloxazolyl])amino)ethoxy]benzyl}thiazolidine-2,4-dione, xxi) 5-{4-[2-(N-methyl-N-(2-[4,5-dimethyloxazolyl])amino)ethoxy]benzyl}thiazolidine-2,4-dione, xxii) 5-{4-[2-(2-pyrimidinylamino)ethoxy]benzyl}thiazolidine-2,4-dione, xxiii) 5-{4-[2-(N-acetyl-N-(2-pyrimidinyl)amino)ethoxy]benzyl}thiazolidine-2,4-dione, xxiv) 5-{4-[2-(N-(2-benzothiazolyl)-N-benzylamino)ethoxy]benzyl}thiazolidine-2,4-dione, xxv) 5-{4-[3-(N-methyl-N-(2-benzoxazolyl)amino)propoxy]benzyl}thiazolidine-2,4-dione, xxvi) 5-{4-[2-(N-methyl-N-(2-pyridyl)amino)ethoxy]benzyl}thiazolidine-2,4-dione (BRL-49653), xxvii) 5-[4-[2-[[[1-(4-biphenylyl)ethylidene]amino]oxy]ethoxy]benzyl]thiazolidine-2,4-dione, xxviii) 5-[4-[2-[[[1-(4-phenylsulfonylphenyl)ethylidene]amino]oxy]ethoxy]benzyl]thiazolidine-2,4-dione, xxix) 5-[4-[2-[[[1-[4-(2-pyridyl)phenyl]ethylidene]amino]oxy]ethoxy]benzyl]thiazolidine-2,4-dione (compound A), xxx) 5-[4-[2-[[[1-[4-(3-pyridyl)phenyl]ethylidene]amino]oxy]ethoxy]benzyl]thiazolidine-2,4-dione, xxxi) 5-[4-[2-[[[1-[4-(4-pyridyl)phenyl]ethylidene]amino]oxy]ethoxy]benzyl]thiazolidine-2,4-dione, xxxii) 5-[4-[2-[[[1-(2-phenyl-5-pyridyl)ethylidene]amino]oxy]ethoxy]benzyl]thiazolidine-2,4-dione, xxxiii) 5-[4-[2-[[[1-(2-methoxy-5-pyridyl)ethylidene]amino]oxy]ethoxy]benzyl]thiazolidine-2,4-dione, xxxiv) 5-[4-[2-[[[1-(2-ethoxy-5-pyridyl)ethylidene]amino]oxy]ethoxy]benzyl]thiazolidine-2,4-dione, xxxv) 5-[4-[2-[[[1-(2-isopropoxy-5-pyridyl)ethylidene]amino]oxy]ethoxy]benzyl]thiazolidine-2,4-dione, xxxvi) 5-[4-[2-[[[1-(2-benzyl-5-pyridyl)ethylidene]amino]oxy]ethoxy]benzyl]thiazolidine-2,4-dione, xxxvii) 4-[4-[2-(2-phenyl-5-methyl-4-oxazolyl)ethoxy]benzyl]-3,5-isoxazolidinedione, xxxviii) 4-[4-[2-(2-phenyl-5-methyl-4-oxazolyl)ethoxy]benzylidene]-3,5-isoxazolidinedione, xxxix) 4-[4-[2-(2-benzothienyl-5-methyl-4-oxazolyl)ethoxy]benzyl]-3,5-isoxazolidinedione, xl) 4-[4-[2-(5-methyl-[2-(2-pyridylthio)ethyl-4-oxazolyl)ethoxy]benzyl]-3,5-isoxazolidinedione, xli) 5-{4-(3-methylimidazo[4,5-b]pyridin-2-ylmethoxy)benzyl}thiazolidine-2,4-dione, xlii) 5-[4-(5-chloro-3-methylimidazo[4,5-b]pyridin-2-ylmethoxy)benzyl]thiazolidine-2,4-dione, xliii) 5-[4-(5-methoxy-3-methylimidazo[4,5-b]pyridin-2-ylmethoxy)benzyl]thiazolidine-2,4-dione, xliv) 5-[4-(5-hydroxy-3-methylimidazo[4,5-b]pyridin-2-ylmethoxy)benzyl]thiazolidine-2,4-dione, xlv) 5-[4-(5-ethoxy-3-methylimidazo[4,5-b]pyridin-2-ylmethoxy)benzyl]thiazolidine-2,4-dione, xlvi) 5-[4-(5-isopropoxy-3-methylimidazo[4,5-b]pyridin-2-ylmethoxy)benzyl]thiazolidine-2,4-dione, xlvii) 5-[4-(1-methylindoline-2-ylmethoxy)benzyl]thiazolidine-2,4-dione, xlviii) 5-[4-(1-methylbenzimidazol-2-ylmethoxy)benzyl]thiazolidine-2,4-dione, xlix) 5-[4-(6-methoxy-1-methylbenzimidazol-2-ylmethoxy)benzyl]thiazolidine-2,4-dione (compound B), l) 5-[4-(5-methoxy-1-methylbenzimidazol-2-ylmethoxy)benzyl]thiazolidine-2,4-dione, li) 5-[4-(1-benzylbenzimidazol-5-ylmethoxy)benzyl]thiazolidine-2,4-dione, lii) 5-[4-(5-hydroxy-1,4,6,7-tetramethylbenzimidazol-2-ylmethoxy)benzyl]thiazolidine-2,4-dione, liii) 5-[4-(5-acetoxy-1,4,6,7-tetramethylbenzimidazol-2-ylmethoxy)benzyl]thiazolidine-2,4-dione, liv) 5-{4-[3-(5-methyl-2-phenyloxazol-4-yl)propionyl]benzyl}thiazolidine-2,4-dione, and lv) 5-[6-(2-fluorobenzyloxy)-2-naphthylmethyl]thiazolidine-2,4-dione or a pharmacologically acceptable salt thereof The compounds of the formulae (I) to (X) of the present invention include more preferably i) 5-[4-(6-hydroxy-2,5,7,8-tetramethylchroman-2-ylmethoxy)benzyl]thiazolidin-2,4-dione (troglitazone), ii) 5-[4-(6-acetoxy-2,5,7,8-tetramethylchroman-2-ylmethoxy)benzyl]thiazolidine-2,4-dione, iii) 5-[4-(6-ethoxycarbonyloxy-2,5,7,8-tetramethylchroman-2-ylmethoxy)benzyl]thiazolidine-2,4-dione, iv) 5-{4-[2-(5-ethyl-2-pyridyl)ethoxy]benzyl}-2,4-thiazolidinedione (pioglitazone), v) 5-[(2-benzyl-3,4-dihydro-2H-benzopyran-6-yl)methyl]thiazolidine-2,4-dione (englitazone), vi) 5-{4-[2-(N-methyl-N-(2-pyridyl)amino)ethoxy]benzyl}thiazolidine-2,4-dione (BRL-49653), vii) 5-[4-[2-[[[1-[4-(2-pyridyl)phenyl]ethylidene]amino]oxy]ethoxy]benzyl]thiazolidine-2,4-dione (compound A), viii) 4-[4-[2-(2-phenyl-5-methyl-4-oxazolyl)ethoxy]benzyl]-3,5-isoxazolidinedione, ix) 5-{4-(3-methylimidazo[4,5-b]pyridin-2-ylmethoxy)benzyl}thiazolidine-2,4-dione, x) 5-[4-(1-methylindolin-2-ylmethoxy)benzyl]thiazolidine-2,4-dione, xi) 5-[4-(1-methylbenzimidazol-2-ylmethoxy)benzyl]thiazolidine-2,4-dione, xii) 5-[4-(6-methoxy-1-methylbenzimidazol-2-ylmethoxy)benzyl]thiazolidine-2,4-dione (compound B), xiii) 5-[4-(5-hydroxy-1,4,6, 7-tetramethylbenzimidazol-2-ylmethoxy)benzyl]thiazolidine-2,4-dione, xiv) 5-{4-[3-(5-methyl-2-phenyloxazol-4-yl)propionyl]benzyl}thiazolidine-2,4-dione, and xv) 5-[6-(2-fluorobenzyloxy)-2-naphthylmethyl]thiazolidine-2,4-dione or a pharmacologically acceptable salt thereof.

The compounds of the formulae (I) to (X) of the present invention include most preferably i) 5-[4-(6-hydroxy-2,5,7,8-tetramethylchroman-2-ylmethoxy)benzyl]thiazolidine-2,4-dione (troglitazone), ii) 5-{4-[2-(5-ethyl-2-pyridyl)ethoxy]benzyl}-2,4-thiazolidinedione (pioglitazone), iii) 5-{4-[2-(N-methyl-N-(2-pyridyl)amino)ethoxy]benzyl}thiazolidine-2,4-dione (BRL-49653), iv) 5-[4-[2-[[[1-[4-(2-pyridyl)phenyl]ethylidene]amino]oxy]ethoxy]benzyl]thiazolidine-2,4-dione (compound A), and v) 5-[4-(6-methoxy-1-methylbenzimidazol-2-ylmethoxy)benzyl]thiazolidine-2,4-dione (compound B)

or a pharmacologically acceptable salt thereof.

The insulin resistance improving compounds used in the present invention are administered in various forms. The administration form is not particularly limited and is determined depending on various kinds of preparation forms, age and sex of the patients, other conditions, the degree of disease, etc. For example, the compound is administered orally in the form of tablets, pills, powders, granules, syrups, solutions, suspensions, emulsions, and capsules. Further, in the case of injections, the compound is intraveneously administered singly or in a mixture with a usual adjuvant solution such as glucose and an amino acid, and further, if necessary, the compound is singly administered intramuscularly, intracutaneously, subcutaneously or intraperitoneally. In the case of suppositories, the compound is intrarectally administered. Oral administration is preferable.

Various kinds of these preparations can be prepared by mixing the known adjuvant usually used in the known pharmaceutical preparation field such as excipients, binders, disintegrants, lubricants, solubilizers, flavors and coating agents with an active compound of the present invention according to the conventional method.

When the present compound is molded into the form of tablets, substances conventionally known in this field as a vehicle can be widely used. Examples include excipients such as lactose, sucrose, sodium chloride, glucose, urea, starch, calcium carbonate, kaolin, crystalline cellulose and silicic acid; binders such as water, ethanol, propanol, single syrup, glucose solution, starch solution, gelatin solution, carboxymethyl cellulose, shellac, methyl cellulose, potassium phosphate, and polyvinyl pyrrolidone; disintegrants such as dry starch, sodium alginate, agar powder, laminaran powder, sodium hydrogencarbonate, calcium carbonate, polyoxyethylenesorbitan fatty acid ester, sodium lauryl sulfate, stearic acid monoglyceride, starch and lactose; disingegration inhibiting agents such as sucrose, stearic acid, cacao butter and hydrogenated oil; absorption accelerating agents such as a quaternary ammonium base and sodium lauryl sulfate; humectants such as glycerin and starch; adsorbing agents such as starch, lactose, kaolin, bentonite and colloidal silicic acid; and lubricants such as purified talc, stearate, boric acid powder and polyethylene glycol. Further, the tablets can be made, if necessary, by the application of a coating film to the tablets, for example, a sugar coating tablet, a gelatin coating tablet, an enteric coated tablet, a film coating tablet, a double layer tablet or a multilayer tablet.

When the present compound is molded into the form of pills, substances conventionally known in this field as a vehicle can be widely used. Examples include excipients such as glucose, lactose, starch, cacao butter, hydrogenated vegetable oil, kaolin and talc; binders such as gum arabic powder, tragacanth powder, gelatin and ethanol; and disintegrants such as laminaran agar.

When the present compound is molded into the form of suppositiories, substances conventionally known in this field as a vehicle can be widely used. Examples include polyethylene glycol, cacao butter, higher alcohols, esters of higher alcohols, gelatin and semi-synthetic glyceride.

In the case where the present compound is prepared as an injection, it is preferable that the solution and suspension are sterilized and are isotonic to blood. When the present compound is formed into such solutions, emulsions and suspensions, substances conventionally used in this field as a diluent can be used. Examples include water, ethyl alcohol, propylene glycol, ethoxylated isostearyl alcohol, polyoxylated isostearyl alcohol and polyoxyethylenesorbitan fatty acid ester. Incidentally, in this case, a sufficient amount of NaCl, glucose or glycerin to prepare the isotonic solution may be contained in a pharmaceutical formulation. Further, usual solubility improvers, buffers and soothing agents may be also added thereto.

Moreover, coloring agents, preservatives, perfumes, flavors, sweeteners and other pharmaceuticals may be contained therein, if necessary.

The amount of the active ingredients contained in the above-mentioned pharmaceutical preparations is not particularly limited and appropriately selected in a wide range, and it is appropriate that the content is usually from 1 to 70% by weight in all compositions, preferably from 1 to 30% by weight.

Further, the autoimmune diseases include those classified into systemic autoimmune diseases such as systemic lupus erythematosus, chronic rheumatoid arthritis, juvenile rheumatoid arthritis, Sjögren's syndrome, systemic scleriasis, mixed connective tissue disease and dermatomyositis; and, diseases classified into organ-specific autoimmune diseases such as Hashimoto's disease, primary myxedema, thyrotoxia, pernicious anemia, ulcerative colitis, autoimmune atrophic gastritis, idiopathic Addison's disease, male infertility, Goodpasture's syndrome, acute progressive glomerular nephritis, myasthenia gravis, multiple myositis, pemphigus vulgaris, bullous pemphigoid, sympathetic ophthalmia, multiple sclerosis, autoimmune hemolytic anemia, idiopathic thrombocytopenic purpura, postmyocardial infarction syndrome, rheumatic fever, lupoid hepatitis, primary biliary cirrhosis, Behcet's syndrome and Crest's syndrome.

In the present invention, the dose of the compound improving insulin resistance will vary depending on the condition of disease, age of the patient, administration methods, etc. In the case of oral administration, for example, it is desirable to administer a compound in an amount of 0.1 mg (preferably 1 mg) as a lower limit and 1000 mg (preferably 500 mg) as an upper limit once to several times a day for an adult human. In the case of intravenous administration, it is desirable to administer a compound in an amount of 0.01 mg (preferably 0.1 mg) as a lower limit and 500 mg (preferably 200 mg) as an upper limit once to several times a day for an adult human depending on the conditions of disease.

The present invention will be described below in more detail by way of Examples, Test examples and Prepration.

EXAMPLES

Example 1

Inhibitory Effect on Lymphocyte Invasion

Streptozotocin was administered intraperitoneally for 5 days to 8-week-old DBA/2 mice at 40 mg/kg to induce autoimmunity to islet β cells. Troglitazone was administered orally by mixing in F2 powdered feed at a concentration of 0.2% for 38 days from the initial day of streptozotocin administration (240 mg/kg/day). Control mice were given only powdered feed for the same period.

Blood samples were collected from the tail vein before the start of streptozotocin administration, during and on the final day of drug administration. The blood samples were separated by centrifugation, and the glucose levels of the collected plasma were measured with a glucose analyzer (Sino-Test Co., Ltd.). Those results are shown in FIG. 1. In the figure, glucose levels (mg/dl) are plotted on the vertical axis, while time (days) is plotted on the horizontal axis.

The mice used in the study were sacrificed following measurement of glucose levels on the final day of troglitazone administration. The pancreas of each animal was excised and fixed with bouian solution. Thin tissue slices were prepared from the pancreas and the degree of lymphocyte invasion into islet cells was observed by light microscope. The percentage (%) of the number of islet cells exhibiting lymphocyte invasion relative to the total number of islet cells was culculated as the degree of lymphocyte invasion. Moreover, the degree of lymphocyte invasion was classified as either 0 to 40% or 40 to 60%. The number of mice classified within each range was illustrated in Table 1 as a percentage (%) relative to the total number of mice in the troglitazone administration group and control group.

TABLE 1

| Study group | Degree of lymphocyte invasion | |
|---|---|---|
| | 0 to 40% | 40 to 60% |
| Control group | 37.5 | 62.5 |
| Troglitazone adminstration group | 100 | 0 |

As is shown in Table 1 above, in contrast to the degree of lymphocyte invasion into islet cells which reached 40 to 60% in 62.5% of the mice in the control group, in the troglitazone group, the degree of lymphocyte invasion into islet cells in all mice was 40% or less. According to these results, troglitazone inhibited invasion of lymphocytes into the target cells.

Moreover, on the basis of the above-mentioned FIG. 1 and Table 1, it was shown that troglitazone inhibits lymphocytes invasion into target cells, and also suppresses the onset of autoimmune disease.

Example 2

Inhibitory Effect on Bone Destruction Induced by Adjuvant Arthritis

The inhibitory effect was determined in a similar manner to that of Winder, et al. (Arthritis Rheum., Vol. 12, p. 472, 1969). Using Lewis rats (females, age 8–10 weeks, body weights: 160–200 g, Japan Charles River) in groups of 5 each, adjuvant (heat-killed *Mycobacterium butyricum*) was injected intradermally into the right hind paw of each rat at 100 μg/0.05 ml/paw to induce arthritis. The rats were orally administered troglitazone at 0.2%, pioglitazone at 0.05% and BRL-49653 at 0.005%, respectively, by mixing in powdered feed until day 20 taking the day of injection of adjuvant to be day 0. Rats in a control group were given powdered feed only during the same period. The rats were sacrificed on day 21. After excising the right hind paw (the injected paw), soft X-rays were taken of each paw to observe and score the state of bone destruction. Bone destruction was scored by evaluating into 5 ranks consisting of 0, 1, 2, 3 and 4, assigning 0 points in the absence of bone destruction (normal) and increasing scores depending on the state of joint destruction, bone destruction, deformation and osteophyte formation. The worst state of such bone disorders was assigned a score of 4. The bone disorders were scored at two locations, the calcaneus and the location extending from the tarsal bones to the metatarsal bones. Thus, the score for each animal was determined by calculating the total score for the two locations and the maximum score was 8 points.

The results are shown in Table 2.

TABLE 2

| Study group | Bone Destruction Score (points) | Bone Destruction Inhibition Rate (%) |
|---|---|---|
| Control group | 7.4 ± 0.4 | |
| Troglitazone administration group | 5.4 ± 0.2* | 27.0 |
| Pioglitazone administration group | 4.4 ± 1.0 | 40.5 |
| BRL-49653 administration group | 4.8 ± 1.2 | 35.1 |

*: P < 0.05 vs. control group

As is clear from Table 2, the troglitazone administration group exhibited significant inhibition of bone destruction as compared with the control group (Wilcoxon test). The pioglitazone and BRL-49653 administration groups also exhibited inhibition of bone destruction.

Example 3

Inhibitory Effect on Lymphocyte Invasion

Streptozotocin was administered intraperitoneally for 5 days to 8-week-old DBA/2 mice at 40 mg/kg to induce autoimmunity of islet β cells. Pioglitazone was administered orally by mixing in F2 powdered feed at a concentration of 0.2% (236 mg/kg/day) for 38 days from the initial day of streptozotocin administration. Mice in the control group were given only powdered feed during the same period.

Figure 2:
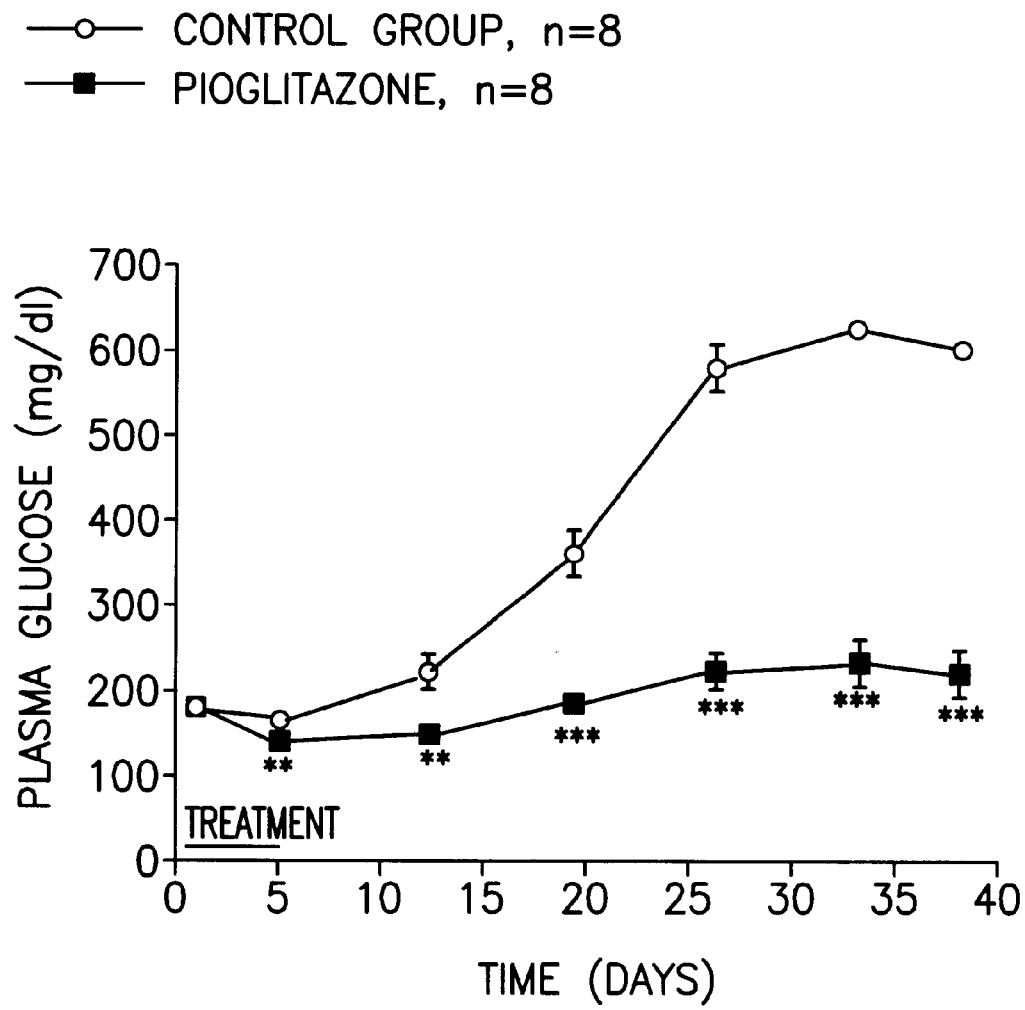
FIG. 2 is a similar graph for reporting the data of Example 3.

Blood samples were collected from the tail vein before the start, during and on the final day of streptozotocin administration. The blood samples were centrifuged to obtain plasma, and the glucose levels of the obtained plasma were measured with a glucose analyzer (Sino-Test Co., Ltd.). Those results are shown in FIG. 2. In the figure, glucose levels (mg/dl) are plotted on the vertical axis, while time (days) is plotted on the horizontal axis.

The mice used in the experiment were sacrificed following measurement of glucose levels on the final day of pioglitazone administration. The pancreas of each animal was excised and fixed with bouian solution. Thin tissue slices were prepared from the pancreas and the degree of lymphocyte invasion into islet cells was observed by a light microscope. The percentage (%) of the number of islet cells exhibiting lymphocyte invasion relative to the total number of islet cells observed was calculated, and this was evaluated as the degree of lymphocyte invasion. Moreover, the degree of lymphocyte invasion was classified as either 0 to 40% or 40 to 60%. The number of mice classified within each range was illustrated in Table 3 as a percentage (%) relative to the total number of mice in the pioglitazone administration group and control groups.

TABLE 3

| Study group | Degree of lymphocyte invasion | |
|---|---|---|
| | 0 to 40% | 40 to 60% |
| Control group | 37.5 | 62.5 |
| Pioglitazone administration group | 100 | 0 |

As is shown in Table 3 above, in contrast to the degree of lymphocyte invasion into islet cells, which reached 40 to 60% in 62.5% of the mice in the control group, in the pioglitazone group, the degree of lymphocyte invasion into islet cells in all mice was 40% or less. According to these results, pioglitazone inhibited invasion of lymphocytes into the target cells.

Moreover, on the basis of the above-mentioned FIG. 2 and Table 3, it was shown that pioglitazone inhibits invasion of lymphocytes into target cells and also suppresses the onset of autoimmune disease.

Example 4

Inhibitory Effect on Lymphocyte Invasion

Streptozotocin was administered intraperitoneally for 5 days to 8-week-old DBA/2 mice at 40 mg/kg to induce autoimmunity of islet β cells. BRL-49653 or Compound A was administered orally by mixing in F2 powdered feed at a concentration of 0.1% (BRL-49653: 125 mg/kg/day, Compound A: 94 mg/kg/day, respectively) for 31 days from the initial day of streptozotocin administration. Control mice were given only powdered feed during the same period.

Figure 3:
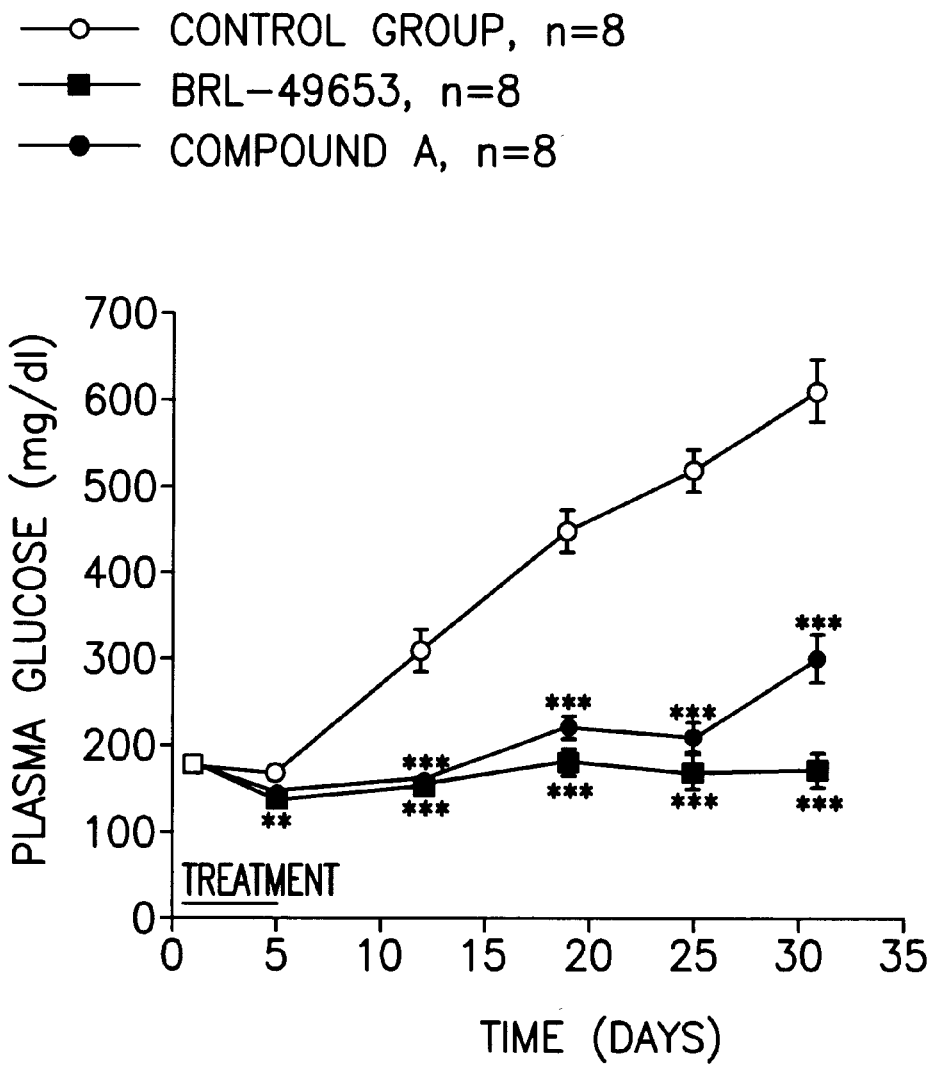
FIG. 3 is a similar graph for reporting the data of Example 4.

Blood samples were collected from the tail vein before the start, during and on the final day of streptozotocin administration. The blood samples were centrifuged to obtain plasma, and the glucose levels of the obtained plasma were measured with a glucose analyzer (Sinotest). Those results are shown in FIG. 3. In the figure, glucose levels (mg/dl) are plotted on the vertical axis, while time (days) is plotted on the horizontal axis.

The mice used in the experiment were sacrificed following measurement of glucose levels on the final day of drug administration. The pancreas of each animal was excised and fixed with bouian solution. Thin tissue slices were prepared from the pancreas and the degree of lymphocyte invasion into islet cells was observed by a light microscope. The percentage (%) of the number of islet cells exhibiting lymphocyte invasion relative to the total number of islet cells observed was calculated, and this was evaluated as the degree of lymphocyte invasion. Moreover, the degree of lymphocyte invasion of each mouse was classified as either 0 to 40% or 40 to 60%. The number of mice classified within each range was represented as shown in Table 4 as a percentage (%) relative to the total number of mice in the BRL-49653 or Compound A and control groups.

TABLE 4

|  | Degree of lymphocyte invasion | |
|---|---|---|
|  | 0 to 40% | 40 to 60% |
| Control group | 55.6 | 44.4 |
| BRL-49653 administration group | 100 | 0 |
| Compound A administration group | 100 | 0 |

As is shown in Table 4 above, in contrast to control mice in which it was observed that 40 to 60% of islet cells were invaded by lymphocytes in 44.4% of total mice, in the BRL-49653 and Compound A groups, the islet cells invaded by lymphocytes were less than 40% in all mice. Namely, BRL-49653 and Compound A inhibited invasion of lymphocytes into the target cells.

Moreover, as is clear from the above-mentioned FIG. 3 and Table 4, it was shown that BRL-49653 and Compound A inhibit invasion of lymphocytes into target cells and also suppresses the onset of autoimmune disease.

Example 5

Inhibitory Effect on Bone Destruction Induced by Adjuvant Arthritis

The inhibitory effect was determined according to the methods of Winder, et al. (Arthritis Rheum., Vol. 12, p. 472, 1969). Using Lewis rats (females, age 8–10 weeks, body weights: 160 to 200 g, Japan Charles River) in groups of 5 each, adjuvant (heat-killed *Mycobacterium butyricum*) was injected intradermally into the sole of the right hind paw of each rat at 100 µg/0.05 ml/paw to induce arthritis. The rats were orally administered Compound A at 0.1% and Compound B at 0.1%, respectively, by mixing in powdered feed until day 20 taking the day of injection of adjuvant to be day 0. Rats in a control group were given powdered feed only during the same period. The rats were sacrificed on day 21. After excising the right hind paw (the injected paw), soft X-rays were taken of each paw to observe and score the state of bone destruction. Bone destruction was scored by evaluating into 5 ranks consisting of 0, 1, 2, 3 and 4, assigning 0 points in the absence of bone destruction (normal) and increasing scores depending on the state of joint destruction, bone destruction, deformation and osteophyte formation. The worst state of bone destruction was assigned a score of 4. Bone destruction was scored at two locations, the calcaneus and the location extending from the tarsal bones to the metatarsal bones. Thus, the score for each animal was determined by calculating the total score for the two locations and the maximum score was 8 points.

The results are shown in Table 5.

TABLE 5

| Study group | Bone Destruction Score (points) | Bone Destruction Inhibition Rate (%) |
|---|---|---|
| Control group | 8.0 ± 0.0 |  |
| Compound A administration group | 6.6 ± 0.7 | 17.5 |
| Compound B administration group | 6.6 ± 0.8 | 17.5 |

As is clear from Table 5, bone destruction tended to be inhibited in the Compound A and Compound B administration groups compared with the control group (Wilcoxon test).

Test Example 1

Acute Toxicity

Acute toxicity was determined in accordance with conventional methods. Namely, after orally administering troglitazone at 300 mg/kg to three ddY mice (males), the animals were observed for 5 days. All animals survived during that time.

Formulation Examples

Formulations containing as their active ingredient an insulin resistance improving substance or its pharmacologically acceptable salt of the present invention can be produced according to, for example, the following methods.

Formulation Example 1

Powder 5 g of troglitazone, 895 of lactose and 100 g of corn starch are mixed in a blender to obtain a powder.

Formulation Example 2
Granules 5 a of troglitazone, 865 g of lactose and 100 g of low-substituted hydroxypropyl cellulose are mixed, followed by addition of 300 g of 10% aqueous hydroxypropyl cellulose and kneading. This mixture is then extruded, formed into granules using a granulating machine and dried to obtain granules.

Formulation Example 3
Capsules 5 g of troglitazone, 115 g of lactose, 58 g of corn starch and 2 g of magnesium stearate are mixed using a V-mixer followed by filling 180 mg of the mixture into no. 3 capsules to obtain capsules.

Formulation Example 4
Tablets 5 g of troglitazone, 90 g of lactose, 34 g of corn starch, 20 g of crystalline cellulose and 1 g of magnesium stearate are mixed in a blender followed by forming into tablets using a tablet making machine to obtain tablets.

Formulation Example 5
Powder 5 g of pioglitazone, 895 g of lactose and 100 g of corn starch are mixed with a blender to obtain a powder.

Formulation Example 6
Granules 5 g of BRL-49653, 865 g of lactose and 100 g of low-substituted hydroxypropyl cellulose are mixed followed by addition of 300 g of 10% aqueous hydroxypropyl cellulose and kneading. This mixture is then extruded, formed into granules using a granulating machine and dried to obtain granules.

Formulation Example 7
Capsules 5 g of Compound A, 115 g of lactose, 58 g of corn starch and 2 g of magnesium stearate are mixed using a V-mixer followed by filling 180 mg of the mixture into no. 3 capsules to obtain capsules.

Formulation Example 8
Tablets 5 g of Compound A, 90 g of lactose, 34 g of corn starch, 20 g of crystalline cellulose and 1 g of magnesium stearate are mixed in a blender followed by forming into tablets using a tablet making machine to obtain tablets.

The insulin resistance improving compounds of the present invention are useful as a preventive or therapeutic agent for autoimmune diseases (excluding type I diabetes).

What is claimed is:

1. A method for the prophylaxis or treatment of an autoimmune disease with the exception of type I diabetes, by inhibiting tissue invasion of target organs by cytotoxic lymphocytes, which method comprises administering to a mammal suffering from or susceptible to said autoimmune disease a pharmacologically effective amount of an anti-autoimmune disease agent thereby counteracting the effects of said tissue invasion, said anti-autoimmune disease agent being an insulin resistance reducing agent.

2. The method according to claim 1, wherein said mammal is a human.

3. A method for the prophylaxis or treatment of an autoimmune disease with the exception of type I diabetes, by inhibiting tissue invasion of target organs by cytotoxic lymphocytes, which method comprises administering to a mammal suffering from or susceptible to said autoimmune disease a pharmacologically effective amount of an anti-autoimmune disease agent thereby counteracting the effects of said tissue invasion, said anti-autoimmune disease agent being an insulin resistance reducing agent, said insulin resistance reducing agent being a compound selected from the group consisting of thiazolidinedione compounds, oxazolidinedione compounds, isoxazolidinedione compounds and oxadiazolidinedione compounds.

4. A method for the prophylaxis or treatment of an autoimmune disease with the exception of type I diabetes, by inhibiting tissue invasion of target organs by cytotoxic lymphocytes, which method comprises administering to a mammal suffering from or susceptible to said autoimmune disease a pharmacologically effective amount of an anti-autoimmune disease agent thereby counteracting the effects of said tissue invasion, said anti-autoimmune disease agent being an insulin resistance reducing agent, said insulin resistance reducing agent being a compound of formula (I):

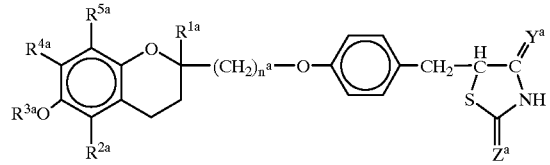

wherein:

$R^{1a}$ and $R^{2a}$ are the same or different and each represents a hydrogen atom or a $C_1$–$C_5$ alkyl group;

$R^{3a}$ is selected from the group consisting of hydrogen atoms, $C_1$–$C_6$ aliphatic acyl groups, $C_6$–$C_8$ cycloalkylcarbonyl groups, benzoyl and naphthoyl groups, said benzoyl groups and said naphthoyl groups being unsubstituted or substituted by a substituent selected from the group consisting of $C_1$–$C_4$ alkyl groups, $C_1$–$C_4$ alkoxy and hydroxy groups, halogen atoms, and amino, mono-$C_1$–$C_4$ alkylamino, di-$C_1$–$C_4$ alkylamino and nitro groups; 4- to 7-membered heterocyclic acyl groups containing from 1 to 3 hetero atoms selected from the hetero atom group consisting of nitrogen, oxygen and sulfur atoms; phenylacetyl groups, phenylpropionyl groups, phenylacetyl and phenylpropionyl groups which are substituted with at least one halogen atom, cinnamoyl groups, $C_2$–$C_7$ alkoxycarbonyl groups and benzyloxycarbonyl groups;

$R^{4a}$ and $R^{5a}$ are the same or different and each is selected from the group consisting of hydrogen atoms, $C_1$–$C_5$ alkyl groups and $C_1$–$C_5$ alkoxy groups, or $R^{4a}$ and $R^{5a}$ together represent a $C_1$–$C_4$ alkylenedioxy group;

$Y^a$ and $Z^a$ are the same or different and each represents an oxygen atom or an imino group; and $n^a$ is an integer of 1 to 3;

or a pharmacologically acceptable salt thereof.

5. A method for the prophylaxis or treatment of an autoimmune disease with the exception of type I diabetes, which method comprises administering to a mammal suffering from or susceptible to said autoimmune disease a pharmacologically effective amount of an anti-autoimmune disease agent, said anti-autoimmune disease agent being an insulin resistance reducing agent, said insulin resistance reducing agent being an oxime compound of formula (V):

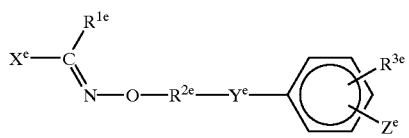

(V)

wherein:
- $R^{1e}$ is selected from the group consisting of hydrogen atoms and straight or branched chain alkyl groups having from 1 to 6 carbon atoms;
- $R^{2e}$ represents a straight or branched chain alkylene group having from 2 to 6 carbon atoms;
- $R^{3e}$ is selected from the group consisting of hydrogen atoms, straight or branched chain alkyl groups having from 1 to 6 carbon atoms, straight or branched chain alkoxy groups having from 1 to 4 carbon atoms, straight or branched chain alkylthio groups having from 1 to 4 carbon atoms, halogen atoms, nitro groups, amino groups, straight or branched chain mono-alkylamino groups having from 1 to 4 carbon atoms, straight or branched chain dialkylamino groups in which said alkyl groups are the same or different and each has from 1 to 4 carbon atoms, aryl groups having from 6 to 10 carbon atoms and aralkyl groups having from 7 to 12 carbon atoms;
- $X^e$ represents an aryl group having from 6 to 10 carbon atoms which is unsubstituted or substituted with 1 to 3 substituents α, defined below, or an aromatic heterocyclic group which is unsubstituted or substituted with 1 to 3 substituents α, defined below;
- said substituent α is selected from the group consisting of: (i) straight or branched chain alkyl groups having from 1 to 6 carbon atoms, (ii) straight or branched chain halogenoalkyl groups having from 1 to 4 carbon atoms, (iii) hydroxy groups, (iv) straight or branched chain acyloxy groups having from 1 to 4 carbon atoms, (v) straight or branched chain alkoxy groups having from 1 to 4 carbon atoms, (vi) straight or branched chain alkylenedioxy groups having from 1 to 4 carbon atoms, (vii) aralkyloxy groups having from 7 to 12 carbon atoms, (viii) straight or branched chain alkylthio groups having from 1 to 4 carbon atoms, (ix) straight or branched chain alkylsulfonyl groups having from 1 to 4 carbon atoms, (x) halogen atoms, (xi) nitro groups, (xii) amino groups, (xiii) straight or branched chain mono-alkylamino groups having from 1 to 4 carbon atoms, (xiv) straight or branched chain dialkylamino groups in which the alkyl groups thereof are the same or different and each has from 1 to 4 carbon atoms, (xv) aralkyl groups having from 7 to 12 carbon atoms, (xvi) aryl groups having from 6 to 10 carbon atoms which are unsubstituted or substituted by a substituent β, defined below, (xvii) aryloxy groups having from 6 to 10 carbon atoms which are unsubstituted or substituted by a substituent β, defined below, (xviii) arylthio groups having from 6 to 10 carbon atoms which are unsubstituted or substituted by a substituent β, defined below, (xix) arylsulfonyl groups having from 6 to 10 carbon atoms which are unsubstituted or substituted by a substituent β, defined below, (xx) arylsulfonylamino groups having from 6 to 10 carbon atoms which are unsubstituted or substituted by a substituent β, defined below, the nitrogen atom of the amino moiety thereof is unsubstituted or substituted with a straight or a branched chain alkyl group having from 1 to 6 carbon atoms, (xxi) aromatic heterocyclic groups, (xxii) aromatic heterocyclyloxy groups, (xxiii) aromatic heterocyclythio groups, (xxiv) aromatic heterocyclysulfonyl groups, and (xxv) aromatic heterocyclysulfonylamino groups, the nitrogen atom of the amino moiety thereof is unsubstituted or substituted with a straight or branched chain alkyl group having from 1 to 6 carbon atoms,
- said substituents β is selected from the group consisting of straight or branched chain alkyl groups having from 1 to 6 carbon atoms, straight or branched chain halogenoalkyl groups having from 1 to 4 carbon atoms, straight or branched chain alkoxy groups having from 1 to 4 carbon atoms, halogen atoms and straight or branched chain alkylenedioxy groups having from 1 to 4 carbon atoms;
- $Y^e$ is selected from the group consisting of oxygen atoms, sulfur atoms and groups of formula $>N-R^{4e}$, wherein $R^{4e}$ is selected from the group consisting of hydrogen atoms, straight or branched chain alkyl groups having from 1- to 6 carbon atoms and straight or branched chain acyl groups having from 1 to 8 carbon atoms; and
- $Z^e$ is selected from the group consisting of a 2,4-dioxothiazolidin-5-ylidenylmethyl group, a 2,4-dioxothiazolidin-5-ylmethyl group, a 2,4-dioxooxazolidin-5-ylmethyl group and a 3,5-dioxooxadiazolidin-2-ylmethyl group;

or a pharmacologically acceptable salt thereof.

6. A method for the prophylaxis or treatment of an autoimmune disease with the exception of type I diabetes, which method comprises administering to a mammal suffering from or susceptible to said autoimmune disease a pharmacologically effective amount of an anti-autoimmune disease agent, said anti-autoimmune disease agent being an insulin resistance reducing agent, said insulin resistance reducing agent being an isoxazolidinedione compound of the formula (VI):

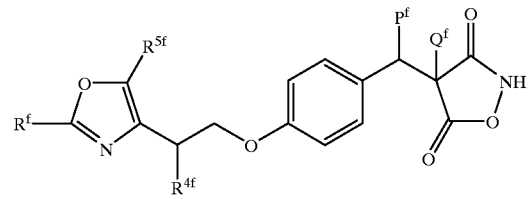

(VI)

wherein:
- $R^f$ is selected from the group consisting of unsubstituted or substituted aromatic hydrocarbon groups, unsubstituted or substituted cycloaliphatic hydrocarbon groups, unsubstituted or substituted heterocyclic groups, unsubstituted or substituted condensed heterocyclic groups and groups of the following formula:

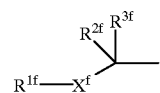

wherein:
- $R^{1f}$ is selected from the group consisting of unsubstituted or substituted aromatic hydrocarbon groups, unsubstituted or substituted cycloaliphatic hydrocarbon groups, unsubstituted or substituted heterocyclic groups and unsubstituted or substituted condensed heterocyclic groups;

$R^{2f}$ and $R^{3f}$ are the same or different and each is selected from the group consisting of hydrogen atoms and alkyl groups; and $X^f$ is selected from the group consisting of oxygen atoms, sulfur atoms and secondary amino groups;

$R^{4f}$ is selected from the group consisting of hydrogen atoms and alkyl groups;

$R^{5f}$ represents an alkyl group; and $P^f$ and $Q^f$ each represent a hydrogen atom or $P^f$ and $Q^f$ taken together represent a bond;

or a pharmacologically acceptable salt thereof.

7. A method for the Prophylaxis or treatment of an autoimmune disease with the exception of type I diabetes, which method comprises administering to a mammal suffering from or susceptible to said autoimmune disease a pharmacologically effective amount of an anti-autoimmune disease agent, wherein said anti-autoimmune disease agent is an insulin resistance reducing agent, the insulin resistance reducing agent being a heterocyclic compound of formula (VII):

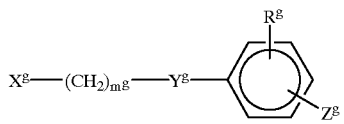

(VII)

wherein:

$X^g$ is selected from the group consisting of indole ring groups, indoline ring groups, azaindole ring groups, imidazopyridine ring groups and imidazopyrimidine ring groups, and said ring groups are unsubstituted or substituted with from 1 to 3 substituents (a) defined below, $Y^g$ represents an oxygen or a sulfur atom;

$Z^g$ is selected from the group consisting of a 2,4-dioxothiazolidin-5-ylidenylmethyl group, a 2,4-dioxothiazolidin-5-ylmethyl group, a 2,4-dioxooxazolidin-5-ylmethyl group, a 3,5-dioxooxazolidin-2-ylmethyl group and an N-hydroxyureidomethyl group;

$R^g$ is selected from the group consisting of hydrogen atoms, straight or branched chain alkyl groups having from 1 to 4 carbon atoms, straight or branched chain alkoxy groups having from 1 to 4 carbon atoms, halogen atoms, hydroxy groups, nitro groups, amino groups which are unsubstituted or substituted with a substituent (b), said substituent (b) is selected from the group consisting of straight or branched chain alkyl groups having from 1 to 8 carbon atoms, straight or branched chain aralkyl groups having from 7 to 11 carbon atoms, aryl groups having from 6 to 10 carbon atoms, straight or branched chain aliphatic acyl groups having from 1 to 11 carbon atoms, aroma-aliphatic acyl groups having from 8 to 12 carbon atoms and aromatic acyl groups having from 7 to 11 carbon atoms, and straight or branched chain aralkyl groups having from 7 to 11 carbon atoms; and $m^g$ is an integer of 1 to 5;

said substituent (a) is selected from the group consisting of straight or branched chain alkyl groups having from 1 to 4 carbon atoms, straight or branched chain alkoxy groups having from 1 to 4 carbon atoms, benzyloxy groups, halogen atoms, hydroxy groups, acetoxy groups, phenylthio groups, straight or branched chain alkylthio groups having from 1 to 4 carbon atoms, trifluoromethyl groups, nitro groups, amino groups which are unsubstituted or substituted by a substituent (b) as defined above, aryl groups having from 6 to 10 carbon atoms which are unsubstituted or substituted with a substituent (c), said substituent (c) is selected from the group consisting of straight or branched chain alkyl groups having from 1 to 4 carbon atoms, straight or branched chain alkoxy groups having from 1 to 4 carbon atoms, halogen atoms, hydroxy groups, nitro groups, phenyl groups, trifluoromethyl groups and amino groups which are unsubstituted or substituted by a substituent (b), as defined above; and straight or branched chain aralkyl groups having from 7 to 11 carbon atoms which are unsubstituted or substituted by substituent (c), as defined above;

or a pharmacologically acceptable salt thereof.

8. A method for the prophylaxis or treatment of an autoimmune disease with the exception of type I diabetes, which method comprises administering to a mammal suffering from or susceptible to said autoimmune disease a Pharmacologically effective amount of an anti-autoimmune disease agent, wherein said anti-autoimmune disease agent is an insulin resistance reducing agent, said insulin resistance reducing agent being a condensed heterocyclic compound of formula (VIII):

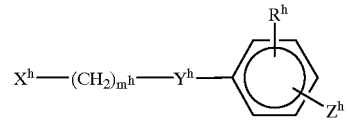

(VIII)

wherein:

$X^h$ represents a benzimidazole ring group which is unsubstituted or substituted with 1 to 5 substituents (a), said substituent (a) is selected from the group consisting of straight or branched chain alkyl groups having from 1 to 4 carbon atoms, straight or branched chain alkoxy groups having from 1 to 4 carbon atoms, benzyloxy groups, halogen atoms, hydroxy groups, acetoxy groups, phenylthio groups, straight or branched chain alkylthio groups having from 1 to 4 carbon atoms, trifluoromethyl groups, nitro groups, amino groups which are unsubstituted or substituted by a substituent (b) as defined below, and aryl groups having from 6 to 10 carbon atoms which are unsubstituted or substituted with a substituent (c), said substituent (c) is a straight or branched chain $C_1$–$C_4$ alkyl group, a straight or branched chain $C_1$–$C_4$ alkoxy group, a halogen atom, a hydroxy group, a nitro group, a phenyl group, a trifluoromethyl group or an amino group which is unsubstituted or substituted by a substituent, (b) or a straight or branched chain $C_7$–$C_{11}$ aralkyl group, $Y^h$ represents an oxygen or a sulfur atom;

$Z^h$ is selected from the group consisting of a 2,4-dioxothiazolidin-5-ylidenylmethyl group, a 2,4-dioxothiazolidin-5-ylmethyl group, 2,4-dioxooxazolidi-5-ylmethyl group, a 3,5- dioxooxadiazolidin-2-ylmethyl group and an N-hydroxyureidomethyl group;

$R^h$ is selected from the group consisting of hydrogen atoms, straight or branched chain alkyl groups having from 1 to 4 carbon atoms, straight or branched chain alkoxy groups having from 1 to 4 carbon atoms, halogen atoms, hydroxy groups, nitro groups, amino groups which are unsubstituted or substituted with a substituent (b), as defined below, and straight or branched chain aralkyl groups having from 7 to 11 carbon atoms, said substituent (b) is selected from the group consisting of straight or branched chain alkyl groups having from 1 to 8 carbon atoms, straight or branched chain aralkyl groups having from 7 to 11 carbon atoms, aryl groups having from 6 to 10 carbon atoms, straight or branched chain aliphatic acyl groups having from 1 to 11 carbon atoms, aroma-aliphatic acyl groups having from 8 to 12 carbon atoms, aromatic acyl groups having from 7 to 11 carbon atoms and straight or branched chain aralkyl groups having from 7 to 11 carbon atoms;

$m^h$ is an integer of 1 to 5;

or a pharmacologically acceptable salt thereof.

9. A method for the prophylaxis or treatment of an autoimmune disease with the exception of type I diabetes, which method comprises administering to a mammal suffering from or susceptible to said autoimmune disease a pharmacologically effective amount of an anti-autoimmune disease agent, said auto-autoimmune disease agent being an insulin resistance reducing agent, said insulin resistance reducing agent being a compound of formula (IX):

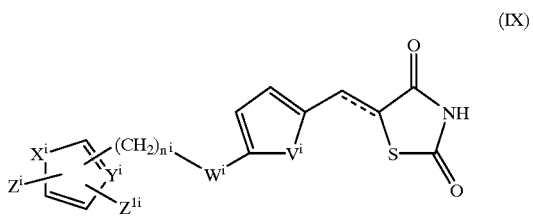

wherein:
the broken line represents a bond or a non-bond;
$V^i$ is selected from the group consisting of —CH═CH—, —N═CH—, —CH═N— and S;
$W^i$ is selected from the group consisting of $CH_2$, CHOH, CO, C═$NOR^i$ and CH═CH;
$X^i$ is selected from the group consisting of S, O, $NR^{1i}$, —CH═N— and —N═CH—;
$Y^i$ is CH or N;
$Z^i$ is selected from the group consisting of hydrogen, $(C_1-C_7)$alkyl, $(C_3-C_7)$cycloalkyl, phenyl, naphthyl, pyridyl, furyl, thienyl and phenyl substituted with one or two substituents selected from the group consisting of $(C_1-C_3)$alkyl, trifluoromethyl and $(C_1-C_3)$alkoxy groups, and fluoro, chloro and bromo atoms, which substituents are the same or different;
$Z^{1i}$ is hydrogen or $(C_1-C_3)$alkyl;
$R^i$ and $R^{1i}$ each independently represent hydrogen or methyl; and
$n^i$ is 1, 2 or 3;

or a pharmacologically acceptable salt thereof.

10. A method for the prophylaxis or treatment of an autoimmune disease with the exception of type I diabetes, which method comprises administering to a mammal suffering from or susceptible to said autoimmune disease a pharmacologically effective amount of an anti-autoimmune disease agent, wherein said anti-autoimmune disease agent is an insulin resistance reducing agent, said insulin resistance reducing agent is a naphthalene compound of formula (X):

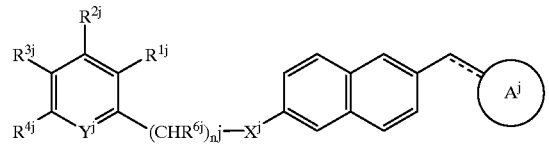

wherein:

 represents

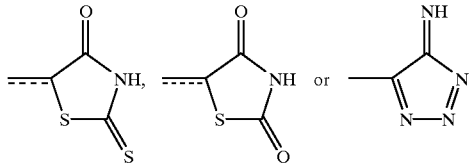

—$X^j$— represents —O— or —S—;
═$Y^j$— represents ═N— or ═$CR^{5j}$—;
$R^{1j}$, $R^{2j}$, $R^{3j}$, $R^{4j}$ and $R^{5j}$ are each independently selected from the group consisting of hydrogen and halogen atoms, and alkyl, aryl, alkoxy, alkoxyalkoxy, aryloxy, alkanoyloxy, arylcarbonyloxy, carboxyl, alkoxycarbonyl, aryloxycarbonyl, carbamoyl, alkylaminocarbonyl, arylaminocarbonyl, amino, alkylamino, alkanoylamino, arylcarbonylamino, ethylenedioxymethyl, formyl, cyano, nitro and trihalomethyl groups;
$R^{6j}$ is selected from the group consisting of hydrogen atoms, unsubstituted or substituted alkyl groups and unsubstituted or substituted aryl groups;
$n^j$ is an integer of 0 to 3; and
the broken line represents a single bond or a non-bond;

or a pharmacologically acceptable salt thereof.

11. The method according to claim 2, wherein said autoimmune disease is a systemic autoimmune disease.

12. The method according to claim 2, wherein said autoimmune disease is an organ-specific autoimmune disease.

13. The method according to claim 2, wherein said autoimmune disease is chronic rheumatoid arthritis.

14. The method according to claim 2, wherein said autoimmune disease is juvenile rheumatoid arthritis.

15. The method of claim 2, wherein said autoimmune disease is systemic lupus erythematosus.

16. The method according to claim 2, wherein said autoimmune disease is Hashimoto's disease.

17. The method according to claim 2, wherein said insulin resistance reducing agent 5-[4-[2-[[[1-[4-(2-pyridyl)phenyl]ethylidene]amino]oxy]ethoxy]benzyl]thiazolidine-2,4-dione, or a pharmacologically acceptable salt thereof.

18. The method according to claim 2, wherein said insulin resistance reducing agent is 5-[4-(6-methoxy-1-methylbenzimidazol-2-ylmethoxy)benzyl]thiazolidine-2,4-dione;

or a pharmacologically acceptable salt thereof.

19. The method according to claim 2, wherein said insulin resistance reducing agent is
4-[4-[2-(phenyl-5-methyl-4-oxazolyl)ethoxy]benzyl]-3,5-isooxazolidinedione.

20. The method according to claim 2, wherein said insulin resistance reducing agent is
5-[6-(2-fluorobenzyioxy)-2-naphthylmethyl]thiazolidine-2,4-dione.

21. The method of claim 3, wherein said mammal is a human.

22. The method of claim 4, wherein said mammal is a human.

23. The method of claim 7, wherein said mammal is a human.

24. The method of claim 8, wherein said mammal is a human.

25. The method of claim 10, wherein said mammal is a human.

26. The method according to claim 21, wherein said autoimmune disease is a systemic autoimmune disease.

27. The method of claim 21, wherein said autoimmune disease is selected from the group consisting of chronic rheumatoid arthritis, juvenile rheumatoid arthritis and systemic lupus erythematosus.

28. The method according to claim 22, wherein said autoimmune disease is systemic autoimmune disease.

29. The method according to claim 22, wherein said autoimmune disease is an organ-specific autoimmune disease.

30. The method of claim 22, wherein said autoimmune disease is selected from the group consisting of chronic rheumatoid arthritis, juvenile rheumatoid arthritis, systemic lupus erythematosus, Hashimoto's disease and ulcerative colitis.

31. The method according to claim 23, wherein said autoimmune disease is a disease which is treatable by an inhibitory action on tissue lymphocyte invasion.

32. The method according to claim 23, wherein said autoimmune disease is a systemic autoimmune disease.

33. The method according to claim 23, wherein said autoimmune disease is an organ-specific autoimmune disease.

34. The method of claim 23, wherein said autoimmune disease is selected from the group consisting of chronic rheumatoid arthritis, juvenile rheumatoid arthritis, systemic lupus erythematosus, Hashimoto's disease and ulcerative colitis.

35. The method according to claim 24, wherein said autoimmune disease is a disease which is treatable by an inhibitory action on tissue lymphocyte invasion.

36. The method according to claim 24, wherein said autoimmune disease is a systemic autoimmune disease.

37. The method according to claim 24, wherein said autoimmune disease is an organ-specific autoimmune disease.

38. The method according to claim 24, wherein said autoimmune disease is selected from the group consisting of chronic rheumatoid arthritis, juvenile rheumatoid arthritis, systemic lupus erythematosus, Hashimoto's disease and ulcerative colitis.

39. The method according to claim 25, wherein said autoimmune disease is a disease which is treatable by an inhibitory action on tissue lymphocyte invasion.

40. The method according to claim 25, wherein said autoimmune disease is a systemic autoimmune disease.

41. The method according to claim 25, wherein said autoimmune disease is an organ-specific autoimmune disease.

42. The method according to claim 25, wherein said autoimmune disease is selected from the group consisting of chronic rheumatoid arthritis, juvenile rheumatoid arthritis, systemic lupus erythematosus, Hashimoto's disease and ulcerative colitis.

43. The method according to claim 2, wherein said insulin resistance reducing agent is a compound selected from the group consisting of
5-[4-(6-hydroxy-2,5,7,8-tetramethylchroman-2-ylmethoxy)benzyl]thiazolidin-2,4-dione,
5-[4-(6-acetoxy-2,5,7,8-tetramethylchroman-2-ylmethoxy)benzyl]thiazolidine-2,4-dione,
5-[4-(6-ethoxycarbonyloxy-2,5,7,8-tetramethylchroman-2-ylmethoxy)benzyl]thiazolidine-2,4-dione,
5-{4-[2-(5-ethyl-2-pyridyl)ethoxy]benzyl}-2,4-thiazolidinedione,
5-[(2-benzyl-3,4-dihydro-2H-benzopyran-6-yl)methyl]thiazolidine-2,4-dione, and
5-{4-[2-(N-methyl-N-(2-pyridyl)amino)ethoxy]benzyl}thiazolidine-2,4-dione;
or a pharmacologically acceptable salt thereof.

44. The method according to claim 2, wherein said insulin resistance reducing agent is a compound selected from the group consisting of
5-[4-(6-hydroxy-2,5,7,8-tetramethylchroman-2-ylmethoxy)benzyl]thiazolidine-2,4-dione,
5-{4-[2-(5-ethyl-2-pyridyl)ethoxy]benzyl}-2,4-thiazolidinedione and
5-{4-[2-(N-methyl-N-(2-pyridyl)amino)ethoxy]benzyl}thiazolidine-2,4-dione;
or a pharmacologically acceptable salt thereof.

45. A method for the prophylaxis or treatment of an autoimmune disease with the exception of type I diabetes by inhibiting tissue invasion of target organs by cytotoxic lymphocytes, which method comprises administering to a mammal suffering from or susceptible to said autoimmune disease a pharmacologically effective amount of an anti-autoimmune disease agent, thereby counteracting the effects of said tissue invasion, said anti-autoimmune disease agent being an insulin resistance reducing agent, said insulin resistance reducing agent being a compound selected from the group consisting of
5-[4-[2-[[[1-[4-(2-pyridyl)phenyl]ethylidene]amino]oxy]ethoxy]benzyl]thiazolidine-2,4-dione,
4-[4-[2-(2-phenyl-5-methyl-4-oxazolyl)ethoxy]benzyl]-3,5-isoxazolidinedione,
5-{4-(3-methylimidazo[4,5-b]pyridin-2-ylmethoxy)benzyl}thiazolidine-2,4-dione,
5-[4-(1-methylindolin-2-ylmethoxy)benzyl]thiazolidine-2,4-dione,
5-[4-(1-methylbenzimidazol-2-ylmethoxy)benzyl]thiazolidine-2,4-dione,
5-[4-(6-methoxy-1-methylbenzimidazol-2-ylmethoxy)benzyl]thiazolidine-2,4-dione,
5-[4-(5-hydroxy-1,4,6,7-tetramethylbenzimidazol-2-ylmethoxy)benzyl]thiazolidine-2,4-dione,
5-{4-[3-(5-methyl-2-phenyloxazol-4-yl)propionyl]benzyl}-thiazolidine-2,4-dione and
5-[6-(2-fluorobenzyloxy)-2-naphthylmethyl]thiazolidine-2,4-dione;
or a pharmacologically acceptable salt thereof.

46. A method for the prophylaxis or treatment of an autoimmune disease with the exception of type I diabetes, which method comprises administering to a mammal suffering from or susceptible to said autoimmune disease a pharmacologically effective amount of an anti-autoimmune disease agent, said anti-autoimmune disease agent being an insulin resistance reducing agent, said insulin resistance reducing agent being a compound selected from the group consisting of 5-[4-[2-[[[1-[4-(2-pyridyl)phenyl]ethylidene]amino]oxy]ethoxy]benzyl]thiazolidine-2,4-dione and 5-[4-(6-methoxy-1-methylbenzimidazol-2-ylmethoxy)benzyl]thiazolidine-2,4-dione;

or a pharmacologically acceptable salt thereof.

47. The method according to claim 21, wherein said insulin resistance reducing agent is a thiazolidinedione compound.

48. The method according to claim 21, wherein said insulin resistance reducing agent is a compound of formula (II):

(II)

[Chemical structure of formula (II)]

or a pharmacologically acceptable salt thereof.

49. The method according to claim 21, wherein said insulin resistance reducing agent is a compound of formula (III):

(III)

[Chemical structure of formula (III)]

wherein:
the broken line represents a single bond or a non-bond;
$n^c$ is 0, 1 or 2;
$X^c$ is selected from the group consisting of O, S, S=O and S(=O)(=O);
$R^c$ is selected from the group consisting of H, $CH_3$ and $C_2H_5$;
$R^{1c}$ is selected from the group consisting of H, $C_5$–$C_7$ cycloalkyl, $C_6$–$C_8$ methylcycloalkyl, pyridyl, thienyl, furyl, naphthyl, p-biphenylyl, tetrahydrofuranyl, tetrahydrothienyl, tetrahydropyranyl, $C_6H_4W^{2c}$, wherein $W^{2c}$ is selected from the group consisting of H, OH, F, Cl, Br, $C_1$–$C_4$ alkyl, $C_1$–$C_4$ alkoxy and $C_1$–$C_4$ thioalkyl, and alk-$W^{1c}$, wherein alk is selected from the group consisting of $C_1$–$C_6$ alkylene, ethylidene and isopropylidene, and $W^{1c}$ is selected from the group consisting of H, OH, $C_1$–$C_4$ alkoxy, $C_1$–$C_4$ thioalkyl, pyridyl, furyl, thienyl, tetrahydrofuranyl, tetrahydrothienyl, naphthyl, $C_5$–$C_7$ cycloalkyl and $C_6H_4W^{2c}$;
$R^{2c}$ is H or $CH_3$;
$R^{3c}$ is selected from the group consisting of H, $C_1$–$C_6$ alkyl, $C_6H_4W^{2c}$ and benzyl; and $R^{4c}$ is H; or
$R^{1c}$ and $R^{2c}$ together form a $C_4$–$C_6$ alkylene, and $R^{3c}$ and $R^{4c}$ each are H; or
$R^{3c}$ and $R^{4c}$ together form a $C_4$–$C_6$ alkylene, and $R^{1c}$ and $R^{2c}$ each are H; or
$R^{2c}$ and $R^{3c}$ together form a $C_3$–$C_4$ alkylene, and $R^{1c}$ and $R^{4c}$ each are H;

or a pharmacologically acceptable salt thereof.

50. The method according to claim 21, wherein said insulin resistance reducing agent is a compound of formula (IV):

(IV)

[Chemical structure of formula (IV)]

wherein:
$A^{1d}$ represents an unsubstituted or substituted aromatic heterocyclic group;
$R^{1d}$ is selected from the group consisting of hydrogen atoms, alkyl groups, acyl groups; aralkyl groups, wherein the aryl moiety thereof is substituted or unsubstituted; and unsubstituted or substituted aryl groups;
$R^{2d}$ and $R^{3d}$ each represent hydrogen or $R^{2d}$ and $R^{3d}$ together form a bond;
$A^{2d}$ represents a benzene ring having not more than 5 substituents in total; and
$n^d$ is an integer of 2 to 6;

or a pharmacologically acceptable salt thereof.

51. The method according to claim 21, wherein said insulin resistance reducing agent is 5-[4-(6-hydroxy-2,5,7,8-tetramethylchroman-2-ylmethoxy)benzyl]thiazolidine-2,4-dione or a pharmacologically acceptable salt thereof.

52. The method according to claim 21, wherein said insulin resistance reducing agent 5-{4-[2-(5-ethyl-2-pyridyl)ethoxy]benzyl}-2,4-thiazolidinedione or a pharmacologically acceptable salt thereof.

53. The method according to claim 21, wherein said insulin resistance reducing agent 5-{4-[2-(N-methyl-N-(2-pyridyl)amino)ethoxy]benzyl}thiazolidine-2,4-dione or a pharmacologically acceptable salt thereof.

54. The method according to claim 6, wherein said autoimmune disease is an organ-specific autoimmune disease.

55. The method according to claim 6, wherein said autoimmune disease is Hashimoto's disease.

56. The method according to claim 9, wherein said insulin resistance reducing agent is 5-[4-[2-[[[1-[-4-(2-pyridyl)phenyl]ethylidene]amino]oxy]ethoxy]benzyl]thiazolidine-2,4-dione, or a pharmacologically acceptable salt thereof.

57. The method according to claim 8, wherein said insulin resistance reducing agent is 5-[4-(6-methoxy-1-methylbenzimidazol-2-ylmethoxy)benzyl]thiazolidine-2,4-dione;

or a pharmacologically acceptable salt thereof.

58. The method according to claim 10, wherein said insulin resistance reducing agent is 5-[6-(2-fluorobenzyloxy)-2-naphthylmethyl]thiazolidine-2,4-dione.

59. The method according to claim 9, wherein said autoimmune disease is an organ-specific autoimmune disease.

60. The method according to claim 9, wherein said autoimmune disease is Hashimoto's disease.

61. The method according to claim 6, wherein said insulin resistance reducing agent is 4-[4-[2-(phenyl-5-methyl-4-oxazolyl)ethoxy]benzyl]-3,5-isooxazolidinedione.

62. A method for the prophylaxis or treatment of Hashimoto's disease comprising administering to a human suffering from or susceptible to Hashimoto's disease a pharmacologically effective amount of an anti-autoimmune disease agent, said anti-autoimmune disease agent being an insulin resistance reducing agent.

63. A method for the prophylaxis or treatment of ulcerative colitis comprising administering to a human suffering from or susceptible to ulcerative colitis a pharmacologically effective amount of an anti-autoimmune disease agent, said anti-autoimmune disease agent being an insulin resistance reducing agent.

64. A method for the prophylaxis or treatment of ulcerative colitis comprising administering to a mammal suffering from or susceptible to ulcerative colitis a pharmacologically effective amount of 5-[4-(6-hydroxy-2,5,7,8-tetrametylchroman-2-ylmethoxy)benzyl]thiazolidine-2,4-dione or a pharmacologically acceptable salt thereof.

* * * * *

UNITED STATES PATENT AND TRADEMARK OFFICE
CERTIFICATE OF CORRECTION

PATENT NO.    : 6,150,371
DATED         : November 21, 2000
INVENTOR(S)   : Fujiwara et al.

It is certified that error appears in the above-identified patent and that said Letters Patent is hereby corrected as shown below:

Column 11,
Line 37, delete "Zerepresents" and insert -- $Z^e$ represents --.

Column 28,
Line 7, delete "(1)" (first occurrence) and insert -- (11) --.
Last line, after "and" insert -- $m^h$ is 1, --.

Column 45,
Line 16, delete "Prophylaxis" and insert -- prophylaxis --.

Column 48,
Line 48, delete "2" and insert -- 5 --.
Line 57, delete "2" and insert -- 5 --.
Line 59, delete "2" and insert -- 5 --.
Line 64, delete "2" and insert -- 5 --.

Column 49,
Line 2, delete "2" and insert -- 5 --.
Line 6, delete "2" and insert -- 5 --.

Signed and Sealed this

Fifth Day of November, 2002

*Attest:*

*Attesting Officer*

JAMES E. ROGAN
*Director of the United States Patent and Trademark Office*